(12) United States Patent
Mihov et al.

(10) Patent No.: US 10,888,531 B2
(45) Date of Patent: *Jan. 12, 2021

(54) DRUG DELIVERY SYSTEM FOR DELIVERY OF ACID SENSITIVITY DRUGS

(71) Applicant: DSM IP Assets, B.V., Heerlen (NL)

(72) Inventors: George Mihov, Echt (NL); Guy Draaisma, Echt (NL); Silvana Rensina Antonnietta Di Silvestre, Echt (NL); Tristan Handels, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/549,127

(22) Filed: Aug. 23, 2019

(65) Prior Publication Data

US 2020/0038337 A1 Feb. 6, 2020

Related U.S. Application Data

(63) Continuation of application No. 15/534,499, filed as application No. PCT/EP2015/080503 on Dec. 18, 2015, now Pat. No. 10,434,071.

(30) Foreign Application Priority Data

Dec. 18, 2014 (EP) .................................. 14198912

(51) Int. Cl.
| | | |
|---|---|---|
| *A61K 9/70* | (2006.01) | |
| *A61K 47/34* | (2017.01) | |
| *A61K 31/5575* | (2006.01) | |
| *A61F 9/00* | (2006.01) | |
| *A61F 9/007* | (2006.01) | |
| *A61K 9/00* | (2006.01) | |
| *C08G 69/36* | (2006.01) | |
| *C08G 69/44* | (2006.01) | |
| *C08L 77/12* | (2006.01) | |
| *A61F 9/008* | (2006.01) | |

(52) U.S. Cl.
CPC ............ *A61K 9/70* (2013.01); *A61F 9/0008* (2013.01); *A61F 9/0017* (2013.01); *A61F 9/00781* (2013.01); *A61K 9/0051* (2013.01); *A61K 31/5575* (2013.01); *A61K 47/34* (2013.01); *C08G 69/36* (2013.01); *C08G 69/44* (2013.01); *C08L 77/12* (2013.01); *A61F 2009/00872* (2013.01); *A61F 2009/00891* (2013.01)

(58) Field of Classification Search
None
See application file for complete search history.

(56) References Cited

U.S. PATENT DOCUMENTS

| | | |
|---|---|---|
| 4,129,594 A | 12/1978 | Baker et al. |
| 4,221,787 A | 9/1980 | Bodor et al. |
| 4,443,563 A | 4/1984 | Dirlikov et al. |
| 4,550,730 A | 11/1985 | Shalaby et al. |
| 4,994,551 A | 2/1991 | Fung et al. |
| 5,057,313 A | 10/1991 | Shih et al. |
| 5,091,560 A | 2/1992 | Rowland |
| 5,100,992 A | 3/1992 | Cohn et al. |
| 5,133,742 A | 7/1992 | Pinchuk |
| 5,206,341 A | 4/1993 | Ibay et al. |
| 5,286,837 A | 2/1994 | Barrows et al. |
| 5,300,114 A | 4/1994 | Gwon et al. |
| 5,449,513 A | 9/1995 | Yokoyama et al. |
| 5,482,700 A | 1/1996 | Deutsch et al. |
| 5,485,496 A | 1/1996 | Lee et al. |
| 5,514,379 A | 5/1996 | Weissleder et al. |
| 5,516,881 A | 5/1996 | Lee et al. |
| 5,554,692 A | 9/1996 | Ross |
| 5,583,206 A | 12/1996 | Snow et al. |
| 5,591,227 A | 1/1997 | Dinh et al. |
| 5,610,241 A | 3/1997 | Lee et al. |
| 5,653,998 A | 8/1997 | Hamann et al. |
| 5,721,131 A | 2/1998 | Rudolph et al. |
| 5,753,234 A | 5/1998 | Lee et al. |
| 5,762,939 A | 6/1998 | Smith et al. |
| 5,770,229 A | 6/1998 | Tanihara et al. |
| 5,849,841 A | 12/1998 | Muhlebach et al. |
| 5,852,155 A | 12/1998 | Bussink et al. |
| 5,858,368 A | 1/1999 | Smith et al. |
| 5,861,387 A | 1/1999 | Labrie et al. |
| 5,874,064 A | 2/1999 | Edwards et al. |
| 5,882,679 A | 3/1999 | Needham |
| 5,885,491 A | 3/1999 | Galan Valdivia et al. |
| 5,904,936 A | 5/1999 | Huille et al. |
| 5,906,934 A | 5/1999 | Grande et al. |
| 5,916,585 A | 6/1999 | Cook et al. |
| 5,919,893 A | 7/1999 | Roby et al. |
| 5,968,794 A | 10/1999 | Samain et al. |
| 5,972,027 A | 10/1999 | Johnson |
| 6,004,573 A | 12/1999 | Rathi et al. |

(Continued)

FOREIGN PATENT DOCUMENTS

| | | |
|---|---|---|
| AU | 2001287015 | 3/2002 |
| AU | 2006204654 | 9/2006 |

(Continued)

OTHER PUBLICATIONS

Asin, et al., Sequential Poly(ester amide)s based on Glycine, Diols, and Dicarboxylic Acids: Thermal Polyesterification verus Interfacial Polyamidation. Characterization of Polymers Containing Stiff Units, J. Polym. Sci. Part A: Polm Chem, 2001, 4283-4293, 39(24).

(Continued)

*Primary Examiner* — Danah Al-Awadi
(74) *Attorney, Agent, or Firm* — Kevin M. Bull

(57) ABSTRACT

The present invention relates to a drug delivery system comprising a core and a shell in which the core comprises a hydrolytically degradable polymer X which polymer backbone comprises pendant ester and acid functionalities and in which the shell comprises a hydrolytic degradable polymer Y. The hydrolytic degradable polymers X and Y are different polymers. Polymer X further comprises amino-acids in the polymer backbone and degrades via zero order degradation kinetics for a period of at least 3 months. Polymer Y degrades via auto-acceleration degradation kinetics.

28 Claims, 15 Drawing Sheets

(56) References Cited

U.S. PATENT DOCUMENTS

| | | |
|---|---|---|
| 6,103,526 A | 8/2000 | Smith et al. |
| 6,111,058 A | 8/2000 | Warzelhan et al. |
| 6,153,252 A | 11/2000 | Hossainy et al. |
| 6,171,610 B1 | 1/2001 | Vacanti et al. |
| 6,210,441 B1 | 4/2001 | Flodin |
| 6,221,997 B1 | 4/2001 | Woodhouse et al. |
| 6,228,391 B1 | 5/2001 | Shimizu et al. |
| 6,245,532 B1 | 6/2001 | Smith et al. |
| 6,299,597 B1 | 10/2001 | Buscemi et al. |
| 6,342,300 B1 | 1/2002 | Bengs et al. |
| 6,352,667 B1 | 3/2002 | English |
| 6,365,160 B1 | 4/2002 | Webb et al. |
| 6,428,807 B1 | 8/2002 | MacFarlan et al. |
| 6,476,204 B1 | 11/2002 | Kim et al. |
| 6,503,538 B1 | 1/2003 | Chu et al. |
| 6,521,431 B1 | 2/2003 | Kiser et al. |
| 6,541,606 B2 | 4/2003 | Margolin et al. |
| 6,660,525 B2 | 12/2003 | Martin et al. |
| 6,703,040 B2 | 3/2004 | Katsarava et al. |
| 6,716,445 B2 | 4/2004 | Won et al. |
| 6,793,938 B2 | 9/2004 | Sankaram |
| 6,830,747 B2 | 12/2004 | Lang et al. |
| 6,982,249 B1 | 1/2006 | Schmaier et al. |
| 6,984,393 B2 | 1/2006 | Amsden |
| 6,994,867 B1 | 2/2006 | Hossainy et al. |
| 7,026,156 B1 | 4/2006 | Clark et al. |
| 7,041,785 B1 | 5/2006 | Recoli et al. |
| 7,122,202 B2 | 10/2006 | Allen et al. |
| 7,220,816 B2 | 5/2007 | Pacetti et al. |
| 7,304,122 B2 | 12/2007 | Chu et al. |
| 7,408,018 B2 | 8/2008 | Chu et al. |
| 7,538,180 B2 | 5/2009 | Pacetti et al. |
| 7,649,022 B2 | 1/2010 | Gomurashvili et al. |
| 7,658,727 B1 | 2/2010 | Fernandes et al. |
| 7,670,829 B2 | 3/2010 | Spagnoli et al. |
| 7,744,861 B2 | 6/2010 | Zhao et al. |
| 7,785,618 B2 | 8/2010 | Elmaleh et al. |
| 7,794,494 B2 | 9/2010 | Sahatjian et al. |
| 7,794,706 B2 | 9/2010 | Carpenter et al. |
| 7,863,406 B2 | 1/2011 | Chu et al. |
| 7,935,493 B2 | 5/2011 | Michnick et al. |
| 8,067,031 B2 | 11/2011 | Daniloff et al. |
| 8,163,269 B2 | 4/2012 | Carpenter et al. |
| 9,963,549 B2 * | 5/2018 | Draaisma .............. C08J 5/18 |
| 2001/0038851 A1 | 11/2001 | Allen et al. |
| 2002/0015720 A1 | 2/2002 | Katsarava et al. |
| 2002/0034532 A1 | 3/2002 | Brodbeck et al. |
| 2002/0044972 A1 | 4/2002 | Davis et al. |
| 2002/0049495 A1 | 4/2002 | Kutryk et al. |
| 2002/0106369 A1 | 8/2002 | Horvath et al. |
| 2002/0147296 A1 | 10/2002 | Teller et al. |
| 2002/0164374 A1 | 11/2002 | Jackson et al. |
| 2002/0165347 A1 | 11/2002 | Fox et al. |
| 2002/0168338 A1 | 11/2002 | Baird |
| 2002/0173586 A1 | 11/2002 | Jeong et al. |
| 2003/0064053 A1 | 4/2003 | Liu et al. |
| 2003/0130185 A1 | 7/2003 | Bar-Or et al. |
| 2003/0175239 A1 | 9/2003 | Margolin et al. |
| 2003/0215454 A1 | 11/2003 | Colb et al. |
| 2003/0217748 A1 | 11/2003 | Giroux |
| 2003/0229393 A1 | 12/2003 | Kutryk et al. |
| 2004/0017387 A1 | 1/2004 | Soltero et al. |
| 2004/0024069 A1 | 2/2004 | Chen et al. |
| 2004/0057958 A1 | 3/2004 | Waggoner, Jr. et al. |
| 2004/0063606 A1 | 4/2004 | Chu et al. |
| 2004/0110285 A1 | 6/2004 | Lendlein et al. |
| 2004/0170685 A1 | 9/2004 | Carpenter et al. |
| 2004/0213759 A1 | 10/2004 | Zalipsky et al. |
| 2004/0213766 A1 | 10/2004 | Francois |
| 2004/0253293 A1 | 12/2004 | Shafiee et al. |
| 2004/0254151 A1 | 12/2004 | Ralston et al. |
| 2004/0258702 A1 | 12/2004 | Blonder et al. |
| 2005/0004378 A1 | 1/2005 | Mane et al. |
| 2005/0013812 A1 | 1/2005 | Dow et al. |
| 2005/0019366 A1 | 1/2005 | Zeldis |
| 2005/0019404 A1 | 1/2005 | Sung et al. |
| 2005/0025752 A1 | 2/2005 | Kutryk et al. |
| 2005/0043787 A1 | 2/2005 | Kutryk et al. |
| 2005/0053667 A1 | 3/2005 | Irvine et al. |
| 2005/0064602 A1 | 3/2005 | Kaufman et al. |
| 2005/0169968 A1 | 8/2005 | Elmaleh et al. |
| 2005/0175583 A1 | 8/2005 | Tamarkin et al. |
| 2005/0208091 A1 | 9/2005 | Pacetti |
| 2005/0216074 A1 | 9/2005 | Sahatjian et al. |
| 2005/0238689 A1 | 10/2005 | Carpenter et al. |
| 2005/0245637 A1 | 11/2005 | Hossainy et al. |
| 2005/0260259 A1 | 11/2005 | Bolotin |
| 2005/0265960 A1 | 12/2005 | Pacetti et al. |
| 2005/0271700 A1 | 12/2005 | DesNoyer et al. |
| 2005/0271701 A1 | 12/2005 | Cottone, Jr. et al. |
| 2005/0287184 A1 | 12/2005 | Hossainy et al. |
| 2005/0288481 A1 | 12/2005 | DesNoyer et al. |
| 2006/0002947 A1 | 1/2006 | Humphreys et al. |
| 2006/0008532 A1 | 1/2006 | Govardhan et al. |
| 2006/0009498 A1 | 1/2006 | Whitcup |
| 2006/0013855 A1 | 1/2006 | Carpenter et al. |
| 2006/0024357 A1 | 2/2006 | Carpenter et al. |
| 2006/0036311 A1 | 2/2006 | Nakayama et al. |
| 2006/0074191 A1 | 4/2006 | DesNoyer et al. |
| 2006/0093842 A1 | 5/2006 | DesNoyer et al. |
| 2006/0115455 A1 | 6/2006 | Reed et al. |
| 2006/0121012 A1 | 6/2006 | Kutryk et al. |
| 2006/0135476 A1 | 6/2006 | Kutryk et al. |
| 2006/0159918 A1 | 7/2006 | Dugan et al. |
| 2006/0177416 A1 | 8/2006 | Turnell et al. |
| 2006/0188469 A1 | 8/2006 | Turnell et al. |
| 2006/0188486 A1 | 8/2006 | Carpenter et al. |
| 2006/0222546 A1 | 10/2006 | Lee et al. |
| 2006/0224331 A1 | 10/2006 | Watson Michnick et al. |
| 2006/0286064 A1 | 12/2006 | Turnell et al. |
| 2007/0042017 A1 | 2/2007 | Kutryk et al. |
| 2007/0055367 A1 | 3/2007 | Kutryk et al. |
| 2007/0066541 A1 | 3/2007 | Hughes et al. |
| 2007/0071790 A1 | 3/2007 | Ameer et al. |
| 2007/0077272 A1 | 4/2007 | Li et al. |
| 2007/0106035 A1 | 5/2007 | Gomurashvili et al. |
| 2007/0128250 A1 | 6/2007 | Katsarava et al. |
| 2007/0134332 A1 | 6/2007 | Turnell et al. |
| 2007/0141100 A1 | 6/2007 | Sung et al. |
| 2007/0141107 A1 | 6/2007 | Kutryk et al. |
| 2007/0156232 A1 | 7/2007 | Kutryk et al. |
| 2007/0160622 A1 | 7/2007 | Turnell et al. |
| 2007/0167605 A1 | 7/2007 | Chu et al. |
| 2007/0191932 A1 | 8/2007 | Kutryk et al. |
| 2007/0196422 A1 | 8/2007 | Kutryk et al. |
| 2007/0213801 A1 | 9/2007 | Kutryk et al. |
| 2007/0282011 A1 | 12/2007 | Gomurashvili et al. |
| 2007/0287987 A1 | 12/2007 | Katsarava et al. |
| 2007/0292476 A1 | 12/2007 | Landis et al. |
| 2007/0299155 A1 | 12/2007 | Carpenter et al. |
| 2008/0020015 A1 | 1/2008 | Carpenter et al. |
| 2008/0050419 A1 | 2/2008 | Katsarava et al. |
| 2008/0057024 A1 | 3/2008 | Zhang et al. |
| 2008/0160089 A1 | 7/2008 | Vitiello et al. |
| 2008/0288057 A1 | 11/2008 | Carpenter et al. |
| 2008/0299174 A1 | 12/2008 | Gomurashvili et al. |
| 2009/0022772 A1 | 1/2009 | Carpenter et al. |
| 2009/0029937 A1 | 1/2009 | Chu et al. |
| 2009/0068743 A1 | 3/2009 | Turnell et al. |
| 2009/0202620 A1 | 8/2009 | Turnell et al. |
| 2009/0232874 A1 | 9/2009 | Chu et al. |
| 2009/0238854 A1 | 9/2009 | Pacetti et al. |
| 2009/0253809 A1 | 10/2009 | Gomurashvili et al. |
| 2010/0004390 A1 | 1/2010 | Turnell et al. |
| 2010/0040664 A1 | 2/2010 | Katsarava et al. |
| 2011/0027379 A1 | 2/2011 | Chu et al. |
| 2011/0104069 A1 * | 5/2011 | Xu ..................... A61K 9/0048 424/9.6 |
| 2011/0137406 A1 | 6/2011 | Carpenter et al. |
| 2012/0027859 A1 | 2/2012 | Turnell et al. |
| 2012/0282299 A1 | 11/2012 | Delamarre et al. |
| 2012/0328706 A1 | 12/2012 | Turnell et al. |
| 2013/0323306 A1 * | 12/2013 | Weber .................. A61K 9/146 424/489 |

(56) References Cited

U.S. PATENT DOCUMENTS

| | | | |
|---|---|---|---|
| 2014/0105957 A1 | 4/2014 | Franken et al. | |
| 2014/0120170 A1* | 5/2014 | Mihov | A61K 47/34 424/501 |
| 2014/0179802 A1* | 6/2014 | Franken | A61K 47/34 514/772.7 |
| 2014/0220099 A1 | 8/2014 | Draaisma et al. | |
| 2015/0038415 A1* | 2/2015 | Zupancich | A61K 47/34 514/11.4 |
| 2015/0216987 A1* | 8/2015 | Thies | C08G 69/44 424/402 |
| 2015/0240387 A1 | 8/2015 | Gillissen-Van Der Vight et al. | |
| 2015/0246001 A1 | 9/2015 | Zupancich et al. | |
| 2015/0328374 A1 | 11/2015 | Mihov et al. | |

FOREIGN PATENT DOCUMENTS

| | | |
|---|---|---|
| CA | 2225792 | 11/1997 |
| CA | 2419429 | 3/2002 |
| CN | 1281355 | 1/2001 |
| CN | 1296852 | 5/2001 |
| CN | 1837259 | 9/2006 |
| CN | 101168595 | 10/2006 |
| DE | 4224401 | 1/1994 |
| EP | 0147780 A3 | 3/1987 |
| EP | 0447719 81 | 11/1993 |
| EP | 0396429 B1 | 7/1996 |
| EP | 0926184 | 6/1999 |
| EP | 0932399 B1 | 1/2006 |
| EP | 1313794 B1 | 11/2006 |
| EP | 1945682 | 7/2008 |
| EP | 2233112 | 9/2010 |
| JP | 2005139139 | 6/2005 |
| JP | 2008027269 | 7/2008 |
| JP | 2008542393 | 11/2008 |
| WO | WO1994004642 | 3/1994 |
| WO | WO1997030104 | 8/1997 |
| WO | WO1998032398 | 7/1998 |
| WO | WO9929303 | 6/1999 |
| WO | WO99029302 | 6/1999 |
| WO | WO199058151 | 11/1999 |
| WO | WO1999061916 | 12/1999 |
| WO | WO2001028591 | 4/2001 |
| WO | WO2001051027 | 7/2001 |
| WO | WO2001091703 | 12/2001 |
| WO | WO2002018477 A2 | 3/2002 |
| WO | WO03024420 | 3/2003 |
| WO | WO2003062298 | 7/2003 |
| WO | WO2004039944 | 5/2004 |
| WO | WO2004040339 | 5/2004 |
| WO | WO2005027906 | 3/2005 |
| WO | WO2005061024 | 7/2005 |
| WO | WO2005097186 | 10/2005 |
| WO | WO2005112587 | 12/2005 |
| WO | WO2005112884 | 12/2005 |
| WO | WO2006050091 | 5/2006 |
| WO | WO2006083874 | 8/2006 |
| WO | WO2006088647 | 8/2006 |
| WO | WO2006108167 | 10/2006 |
| WO | WO2006132950 | 12/2006 |
| WO | WO2007035938 A2 | 3/2007 |
| WO | WO2007050415 | 5/2007 |
| WO | WO2007067744 | 6/2007 |
| WO | WO2007089870 | 8/2007 |
| WO | WO2007089931 | 8/2007 |
| WO | WO2007130477 | 11/2007 |
| WO | WO2007133616 | 11/2007 |
| WO | WO2008048298 | 4/2008 |
| WO | WO2008157254 | 12/2008 |
| WO | WO2009012449 A1 | 1/2009 |
| WO | WO2009015143 | 1/2009 |
| WO | WO2009026543 | 2/2009 |
| WO | WO20100045241 | 4/2010 |
| WO | WO2010111449 | 9/2010 |
| WO | WO2011045443 A1 | 4/2011 |
| WO | WO2011146483 | 11/2011 |
| WO | WO2012150255 | 11/2012 |
| WO | WO2012175746 | 12/2012 |
| WO | WO2012175748 | 12/2012 |
| WO | WO14064196 | 5/2014 |
| WO | WO2014064196 | 5/2014 |
| WO | WO2007038246 | 4/2017 |
| WO | WO2005118681 | 12/2017 |

OTHER PUBLICATIONS

Becker et al., Prevention of Postoperative Abdominal Adhesions by a Sodium Hyaluronate-Based Bioresorbable Membrane: A Prospective, Randomized, Double-Multicenter Study, J. Am. Coll. Surg. 1996, pp. 297-306, 183.

Eccleston et al, pH-responsive pseudo-peptides for cell membrane disruption, Journai of Controlled Release, 2000, pp. 297-307, vol. 69, No. 2.

Eccleston et al., Synthetic routes to responsive polymers, Reactive & Functional Polymers, 1998, pp. 147-161, vol. 42, No. 2.

Furchgott and Zawadzki, The obligatory role of endothelial cells in the relaxation of arterial smooth muscle by acetylcholine, Inature, 1980, pp. 373-376, 388.

Gautier et al, Alkylated poly(L-lysine citramide) as modeis to investigate the ability, Journal of Controlled release, 1999, pp. 235-247, vol. 60, No. 2-3.

Gomurashvili , et al, Amino Acid Based Bioanalogous Polymers. Synthesis and Study of New Poly(Ester Amide)S Composed of Hydrophobic α-Amino Acids and Dianhydrohexitoles, J.M.S.—Pure Appl. Chem, 2000, pp. 215-227, A37(3).

Gomurashvili, et al., From Drug-Eluting Stents to Biopharmaceuticals: Poly(ester amide) a Versatile New Bioabsorable Biopolymer. In: Polymers for Biomedical Applications, ACS Symposium Series; American Chemical Society, 2008, pp. 10-26, Chapter 2.

Guo, et al., Synthesis and Characterization of Novel Biodegradable Unsaturated Poly(ester amide)/Poly(ethylene glycol) Diacrylate Hydrogels, Journal of Polymer Science: Part A: Polymer Chemistry, 2005, pp. 3932-3944, 43.

Huang, et al., Biodegradable Polymers: Chymotrypsin Degradationi of a Low Molecular Weight Poly(ester-Urea) Containing Phenylalanine, J. Appl. Polym. Sci, 1979, pp. 429-437, 23.

Kartvelishvili, et al., Amino acid based bioanalogous polymers. Novel regular poly(ester urethane)s and poly(ester ureas based on bis(L-phenylalanine) α, ω-alkylene diesters, Macromol. Chem. Phys, 1997, pp. 1921-1932, 198.

Kropp, et al, Biocompatibility of Poly(ester amide) (PEA) Microfibrils in Ocular Tissues, Polymers, 2014, pp. 243-260, vol. 6.

Qian, et al., Preparation of biodegradable polyesteramide microspheres, Colloid Polym. Sci, 2004, pp. 1083-1088, 282.

Saotome et al, Novel Enzymatically Degradable Polymers Comprising a-Amino Acid, 1,2-Ethanediol, and Adipic Acid, Chemistry Letters, 1991, pp. 21-24, No Volume.

Tsitlanadze et al., Biodegradation of amino-acid-based poly(ester amide)s: in vitro weight loss and preliminary in vivo studies, Journal of Biomaterials Science, Jan. 1, 2004, 24 Pages, vol. 15.

Yokoe et al, Biodegradable Polymers Based an Renewabie Resources. VII. Novei Random and Alternating Copolycarbanates from 1,4:3,6-Dianhydrohexitols and Aliphatic Diols, Journal of Polymer Science: Part A: Polymer Chemistry, 2003, pp. 2312-2331, 41.

Final Office Action in U.S. Appl. No. 14/432,349, dated Apr. 12, 2017.

Final Office Action in U.S. Appl. No. 14/128,839, dated May 19, 2017.

\* cited by examiner

DRUG DELIVERY SYSTEM FOR DELIVERY OF ACID SENSITIVITY DRUGS

This application is a Continuation of U.S. patent application Ser. No. 15/534,499, now U.S. Pat. No. 10,434,071; which is a US National Phase application of International Application PCT/EP2015/080503, filed 18 Dec. 2015, which designated the US and claims priority to European Patent Application No. EP14198912.9, filed 18 Dec. 2014, the entire contents of each of which are hereby incorporated by reference.

The present invention relates to a drug delivery system comprising a core and a shell. The present invention further relates to a fiber comprising a core and a shell. The present invention also relates to a process for the manufacturing of the drug delivery system.

The present invention in particular relates to the field of sustained drug delivery to the eye and more particularly to the treatment and/or prevention of raised intraocular pressure, such as that associated with glaucoma.

Glaucoma is one of the leading causes of blindness in the developed countries of the world. The chief pathophysiological feature of glaucoma is raised intraocular pressure. Surgery and/or drugs intended to lower intraocular pressure are the most common treatments for glaucoma. The principal pharmaceutical treatment in use today is the topical administration of drug solutions via eye drops. The drugs are for example miotics (e.g., pilocarpine, carbachol and echothiophate), which open the trabecular meshwork to increase the rate of fluid flow out of the eye.

Self-administration of eye drops often results in a substantial portion of the drop being lost due to overflow. A substantial portion of the drug solution that is delivered to the ocular surface is then immediately washed away by tears. Moreover, that portion of the drug which does penetrate the cornea results in an initial peak tissue concentration, followed by a gradual decrease, so that before the next administration of the eye drops the tissue concentration may be below the concentration needed to create the intended pharmacological effect. The variable and intermittent topical administration of eye drops, combined with the vagaries of patient compliance with the prescribed regimen, result in cycles of high and low concentrations of topical anti-glaucoma agents in the eye, and the possible cycling of intraocular pressure. As a result of this the optic nerve might get irreversibly damaged over time. The ideal treatment would maintain a therapeutically effective amount of drug in the eye at all times.

Drug delivery systems comprising a core and a shell are known in the art. In EP2233112, a drug delivery device is disclosed shaped and sized for injection and comprising a core including one or more drugs; and a polymeric skin at least partially surrounding the core, whereby the skin comprises a polymer such as poly(vinyl acetate), poly(caprolactone), polyethylene glycol, poly(dl-lactide-co-glycolide), ethylene vinyl acetate polymer, poly(lactic acid) (PLA), poly(glycolic acid) (PGA), polyalkyl cyanoacralate, polyurethane or nylon.

A drug delivery system intended to provide sustained release of a drug should provide a controlled release, i.e., it should release the drug in a relatively linear manner over time, so as to maintain not only prolonged release but also a relatively constant and therapeutically effective concentration of the drug. The duration of release should be sufficiently long so that the insertion of the device is not inconveniently frequent. Depending on the condition to be treated, such devices may provide for controlled release over a period of weeks, months or even years. This is of particular importance (benefit) for chronic patient conditions such as glaucoma.

In case that the drug is dispersed in the polymer matrix, the drug is released as it dissolves and diffuses out of the matrix. In devices based on the polymer matrix, the drug dispersed in the matrix may be present either in dissolved or dispersed form. Release follows Fickian kinetics from devices where the drug is dissolved. When the drug is dispersed in the polymer matrix, it is released according to $t^{1/2}$ kinetics until the concentration in the matrix falls below the saturation value, at which point the release rate slows down and Fickian release is observed. For these reasons, the maintenance of the drug concentration within the therapeutic window for a long period of time can be difficult to achieve with polymer matrix systems.

In some drug delivery systems, diffusion through the polymer matrix is extremely slow, and drugs are intended to be released only as the polymer matrix is degraded. It has proven to be difficult to use this approach to a linear release.

It is an object of the present invention to provide a drug delivery system that meets a linear release over time, that meets a prolonged release, and that meets a relatively constant and therapeutically effective concentration of drug.

In particular, it is an object of the present invention to provide an improved method for treating and/or preventing glaucoma and other indications associated with raised intraocular pressure by administering drugs to the eye in a manner that avoids the problems of variable drug concentration associated with topical administration without causing systemic side effects.

The object of the present invention is achieved in that a drug delivery system is provided comprising a core and a shell in which the core comprises a hydrolytically degradable polymer X which polymer backbone comprises pendant ester and acid functionalities and in which the shell comprises a hydrolytic degradable polymer Y.

Preferably the hydrolytic degradable polymers X and Y are different polymers.

Surprisingly it has been found that the drug delivery system according to the present invention not only provides a prolonged release but also a relatively constant release of a therapeutically effective concentration of the drug. Moreover, it has been surprisingly found that the hydrolytically degradable polymer X does not built an acidic micro-climate in the polymer matrix during the polymer degradation despite that the hydrolysis of polymer X results in the generation of carboxyl groups.

The lack of acidic micro-climate is beneficial for maintaining the structure of acid-sensitive drugs which means for maintaining its stability. For example, ocular hyperemia and other side effects were observed in the early development of latanoprost and triggered the development of the prodrug (Latanoprost ester) structure in clinical use today. Latanoprost is a prostaglandin F2a analogue. Specifically, Latanoprost is a prostanoid selective FP receptor agonist that is believed to reduce the intraocular pressure (IOP) by increasing the outflow of aqueous humor. Elevated IOP represents a major risk factor for glaucomatous field loss. The higher the level of IOP, the greater the likelihood of optic nerve damage and visual field loss. Latanoprost is an isopropyl ester and the ester was found to improve the ocular penetration and consequently ocular hypotensive potency. It is important that the ester form is stable enough not to be rapidly de-esterified, yet hydrolyzed by tissue esterases to have a full intraocular hypotensive effect. Thus, drug structure preservation is essential for high bioavailability (drug transport through the tissue and efficacy at low dosage) and to diminish side effects such as conjunctival hyperemia and ocular irritation.

Beside the remaining stability of acid sensitive drugs it has moreover been found that the drug delivery system according to the present invention provides the release of a constant dose of drug as from day 10 over the next 3 months. This is of utmost importance for the treatment of glaucoma and other indications associated with raised intraocular pressure and avoids the problems of a variable drug concentration. The goal of the present drug delivery system is to maintain drug levels within a therapeutic range and ideally a constant and predictable level. In order to achieve relatively constant levels, the drugs should be released from a delivery system at a rate that varies very little over the time.

It has been found that the hydrolytic polymer X degrades via pseudo zero order degradation kinetics for a period of at least 3 months. A zero order reaction has a rate that is independent of the concentration of the reactant(s) and reaction products. Increasing the concentration of the reaction products will not speed up the rate of the reaction i.e. the amount of substance reacted is proportional to the time. Usually biodegradable polymers degrade via auto-accelerated kinetics since degradation yields carboxyl acid groups which further catalyze the degradation. Despite the degradation of polymer X in the present invention yields carboxyl groups the degradation does not follow auto-accelerated kinetics.

The polymer backbone comprises pendant ester and acid functionalities. Preferably it comprises at least 15% acid groups based on the total pendant functionalities. Polymer X preferably also comprises amino-acids in the polymer backbone. Most preferably polymer X is a polyesteramide copolymer. The polyesteramide copolymer preferably comprises building blocks A and B in the backbone, wherein Block A is L-Lysine-H (=Lysine free carboxylic groups) and block B is L-lysine-benzyl (=Lysine benzyl ester).

Polyesteramides in which both L-Lysine-H as well L-lysine-benzyl are present, (hereinafter referred to as PEA-X) are disclosed in WO-A-2012175746. These PEA-X polymers provide a sustained release of bioactive agents and degrade hydrolytically at physiological conditions via bulk erosion mechanism.

It seems that lysine free carboxylic groups and acidic species generated during the degradation are in a right balance to catalyze bond cleavage along the polyesteramide chain but not compromising material performance properties at physiological conditions. Furthermore, the pendant carboxyl groups prevent the auto-acceleration of the polymer degradation process which contributes for a more controlled and prolonged material biodegradation.

In a preferred embodiment the polyesteramide copolymer (PEA-X) is a random copolymer. Most preferably the polyesteramide copolymer (PEA-X) comprises structural formula I;

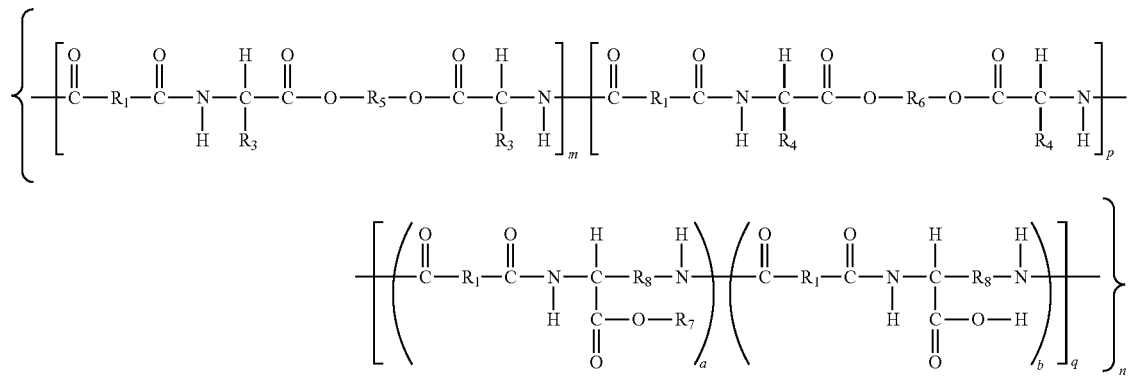

Formula I wherein
m+p varies from 0.9-0.1 and q varies from 0.1 to 0.9;
m+p+q=1 whereby m or p could be 0;
n varies from 5 to 300;
$R_1$ is independently selected from the group consisting of $(C_2$-$C_{20})$ alkylene, $(C_2$-$C_{20})$ alkenylene and combinations thereof;
$R_3$ and $R_4$ in a single backbone unit m or p, respectively, are independently selected from the group consisting of hydrogen, $(C_1$-$C_6)$alkyl, $(C_2$-$C_6)$alkenyl, $(C_2$-$C_6)$alkynyl, $(C_6$-$C_{10})$aryl, $(C_1$-$C_6)$alkyl, —$(CH_2)$SH, —$(CH_2)_2$S$(CH_3)$, —$CH_2$OH, —CH(OH)$CH_3$, —$(CH_2)_4$NH$_3$+, —$(CH_2)_3$NHC(=NH$_2$+)NH$_2$, —$CH_2$COOH, —$CH_2$—CO—NH$_2$, —$CH_2CH_2$—CO—NH$_2$, —$CH_2CH_2$COOH, $CH_3$—$CH_2$—CH($CH_3$)—, ($CH_3$)$_2$—CH—$CH_2$—, $H_2$N—$(CH_2)_4$—, Ph-$CH_2$—, CH=C—$CH_2$—, HO-p-Ph-$CH_2$—, ($CH_3$)$_2$—CH—, Ph-NH—, NH—$(CH_2)_3$—C—, NH—CH=N—CH=C—$CH_2$—;
$R_5$ is selected from the group consisting of $(C_2$-$C_{20})$alkylene, $(C_2$-$C_{20})$alkenylene, alkyloxy or oligoethyleneglycol;
$R_6$ is selected from bicyclic-fragments of 1,4:3,6-dianhydrohexitols of structural formula (II); cycloalkyl fragments such as 1,4-cyclohexane diol derivative, aromatic fragments or heterocyclic fragments such as hexose derived fragments;

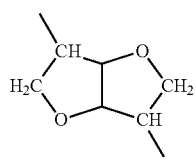

Formula II $R_7$ is selected from the group consisting of $(C_6$-$C_{10})$ aryl $(C_1$-$C_6)$ alkyl;

$R_8$ is —$(CH_2)_4$—; whereby a is at least 0.05, b is at least 0.05 and a+b=1.

In the following embodiments n in the polyesteramide copolymer of Formula (I), preferably varies from 50-200, a may be at least 0.15, more preferably at least 0.5, most preferably 0.75, even more preferably at least 0.8.

In one embodiment the polyesteramide copolymer according to Formula (I) comprises p=0 and m+q=1 whereby m=0.75, a=0.5 and a+b=1, $R_1$ is $(CH_2)_8$, $R_3$ is —$(CH_3)_2$—CH—$CH_2$—, $R_5$ is hexyl, $R_7$ is benzyl and $R_8$ is —$(CH_2)_4$—. This polyesteramide is referred to as PEA-I-H/Bz 50% H.

In another preferred embodiment the polyesteramide copolymer according to Formula (I) comprises m+p+q=1, q=0.25, p=0.45 and m=0.3 whereby a is 0.5 and a+b=1 and whereby $R_1$ is —$(CH_2)_8$; $R_3$ and $R_4$ respectively are —$(CH_3)_2$—CH—$CH_2$—, $R_5$ is selected from the group consisting of $(C_2-C_{20})$alkylene, $R_6$ is selected from bicyclic-fragments of 1,4:3,6-dianhydrohexitols of structural formula (II); $R_7$ is benzyl and $R_8$ is —$(CH_2)_4$. This polyesteramide is referred to as PEA-III-H/Bz 50% H.

In a further preferred embodiment the polyesteramide copolymer according to Formula (I) comprises m+p+q=1, q=0.25, p=0.45 and m=0.3 whereby a is 0.25 and a+b=1 and whereby $R_1$ is —$(CH_2)_8$; $R_3$ and $R_4$ respectively are —$(CH_3)_2$—CH—$CH_2$—, $R_5$ is selected from the group consisting of $(C_2-C_{20})$alkylene, $R_6$ is selected from bicyclic-fragments of 1,4:3,6-dianhydrohexitols of structural formula (II); $R_7$ is benzyl and $R_8$ is —$(CH_2)_4$. This polyesteramide is referred to as PEA-III-H/Bz 75% H.

In a still further preferred embodiment the polyesteramide copolymer according to Formula (I) comprises m+p+q=1, q=0.25, p=0.45 and m=0.3 whereby a is 0.75 and a+b=1, $R_1$ is —$(CH_2)_8$; $R_4$ is $(CH_3)_2$—CH—$CH_2$—, $R_7$ is benzyl, $R_8$ is —$(CH_2)_4$—, $R_5$ is selected from the group consisting of $(C_2-C_{20})$alkylene and $R_6$ is selected from bicyclic fragments of 1,4:3,6-dianhydrohexitols of structural formula (II). This polyesteramide is referred to as PEA-III-H/Bz 25% H.

In a yet further preferred embodiment the polyesteramide copolymer according to Formula (I) comprise m+p+q=1, q=0.1, p=0.30 and m=0.6 whereby a=0.5 and a+b=1. $R_1$ is —$(CH_2)_4$; $R_3$ and $R_4$ respectively, are $(CH_3)_2$—CH—$CH_2$—; $R_5$ is selected from the group consisting of $(C_2-C_{20})$ alkylene, $R_7$ is benzyl, $R_8$ is —$(CH_2)_4$— and $R_6$ is selected from bicyclic-fragments of 1,4:3,6-dianhydrohexitols of structural formula (II). This polyesteramide is referred to as PEA-II-H/Bz50% H.

As used herein, the term "alkyl" refers to a monovalent straight or branched chain hydrocarbon group including methyl, ethyl, n-propyl, isopropyl, n-butyl, isobutyl, tert-butyl, n-hexyl, and the like.

As used herein, the term "alkylene" refers to a divalent branched or unbranched hydrocarbon chain such as —$CH_2$—, —$(CH_2)_2$—, —$(CH_2)_3$—, —$(CH_2)4$-, —$(CH2)$5- and the like.

As used herein, the term "alkenyl" refers to a monovalent straight or branched chain hydrocarbon group containing at least one unsaturated bond in the main chain or in a side chain.

As used herein, "alkenylene", refers to structural formulas herein to mean a divalent branched or unbranched hydrocarbon chain containing at least one unsaturated bond in the main chain or in a side chain.

As used herein, "alkynyl", refers to straight or branched chain hydrocarbon groups having at least one carbon-carbon triple bond.

The term "aryl" is used with reference to structural formulas herein to denote a phenyl radical or an ortho-fused bicyclic carbocyclic radical having about nine to ten ring atoms in which at least one ring is aromatic. Examples of aryl include, but are not limited to, phenyl, naphthyl, and nitrophenyl.

The term biodegradable" refers to material which is capable of being completely or substantially degraded or eroded when exposed to an in vivo environment or a representative in vitro. A polymer is capable of being degraded or eroded when it can be gradually broken-down, resorbed, absorbed and/or eliminated by, for example, hydrolysis, enzymolysis, oxidation, metabolic processes, bulk or surface erosion, and the like within a subject. The terms "bioabsorbable" and "biodegradable" are used interchangeably in this application.

At least one of the alpha-amino acids used in the polyesteramide copolymers according to formula (I) is a natural alpha-amino acid. For example, when the R3s or R4s are benzyl the natural alpha-amino acid used in synthesis is L-phenylalanine. In alternatives wherein the R3 or R4 are —$CH_2$—$CH(CH_3)_2$, the co-polymer contains the natural amino acid, leucine. By independently varying the $R_3$ and $R_4$ within variations of the two co-monomers as described herein, other natural alpha-amino acids can also be used, e.g., glycine (when the $R_3$ or $R_4$ are H), alanine (when the $R_3$ or $R_4$ are $CH_3$), valine (when the $R_3$ or $R_4$ are —$CH(CH_3)_2$, isoleucine (when the $R_3$ or $R_4$ are —$CH(CH_3)$—$CH_2$—$CH_3$), phenylalanine (when the $R_3$ or $R_4$ are $CH_2$—$C_6H_5$), lysine (when the $R_3$ or $R_4$ $(CH_2)_4$—$NH_2$); or methionine (when the $R_3$ or $R_4$ are —$(CH_2)_2S(CH_3)$, and mixtures thereof.

The polyesteramide co-polymers of Formula (I) preferably have an average number molecular weight (Mn) ranging from 15,000 to 200,000 Daltons. The polyesteramide co-polymers described herein can be fabricated in a variety of molecular weights and a variety of relative proportions of the m, p, and q units in the backbone. The appropriate molecular weight for a particular use is readily determined by one skilled in the art. A suitable Mn will be in the order of about 15,000 to about 100,000 Daltons, for example from about 30,000 to about 80,000 or from about 35,000 to about 75,000. Mn is measured via GPC in THF with polystyrene as standard.

The basic polymerization process of polyesteramides is based on the process described by G. Tsitlanadze, et al. J. Biomater. Sci. Polym. Edn. (2004) 15:1-24, however different building blocks and activating groups were used.

The polyesteramides of Formula (I) are for example synthesized as shown in scheme 1; via solution polycondensation of para-toluene sulfonate di-amines salts (X1, X2, X3) with activated di-acids (Y1). Typically dimethylsulfoxide or dimethylformamide is used as solvent. Typically as a base triethylamide is added, the reaction is carried out under an inert atmosphere at 60° C. for 24-72 hours under constant stirring. Subsequently the obtained reaction mixture is purified via a water precipitation followed by an organic precipitation and filtration. Drying under reduced pressure yields the polyesteramide.

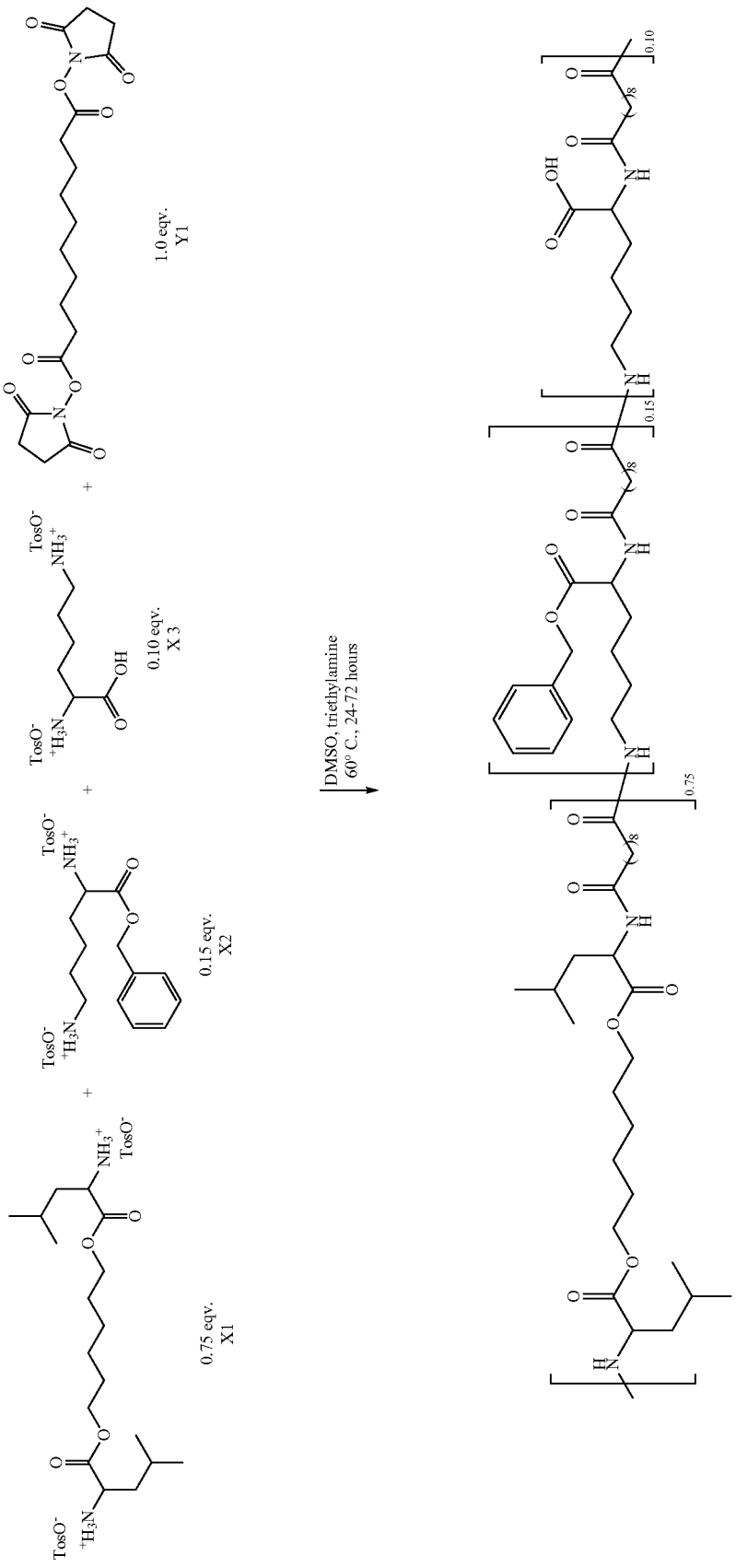

The drug delivery system according to the present invention comprises a shell comprising a hydrolytic degradable polymer Y. Preferably polymer Y degrades via auto-acceleration kinetics. Typically, hydrolytic degradable polymers comprise multiple ester bonds along the polymer chain which are primarily responsible for the hydrolytic degradation properties. The hydrolytic degradation process starts with cleavage of ester bonds which results of generation of free carboxylic groups. These carboxylic groups catalyze further the hydrolysis, speeding up the degradation process and generation of new carboxylic groups. Overall the carboxylic groups appear a chemical reaction product and their concentration increases over time. On the other hand carboxylic groups appear a catalyst of the hydrolytic process which accelerates the degradation. A shell prepared of a such polymer could be designed to degrade relatively slowly at the beginning suppressing the burst release of the drug from the drug delivery system core. Later, when barrier properties of the shell are no longer needed, the accelerating degradation rate will result in a quick erosion of the shell enchanting the drug release from the core polymer.

The hydrolytically degradable polymer Y is preferably a polyester which is a class of polymers characterized by ester linkages in the backbone, such as poly(lactic acid) (PLA), poly(glycolic acid) (PGA), poly(lactide-co-glycolide) (PLGA), etc. PLGA is one of the most commonly used degradable polymer in developing drug delivery systems. PLGA is synthesized by ring-opening copolymerization of two different monomers, the cyclic dimmers (1,4-dioxane-2,5-diones) of glycolic acid and lactic acid. PLGA degrades via hydrolysis of its ester linkages in the presence of water.

The drug delivery system according to the present invention comprises a core and a shell, preferably the drug delivery system is a microparticle, nanoparticle, rod, fiber or implant. More preferably the drug delivery system is a fiber.

Typically, the average diameter of the fibers is between 50 μm and 1000 μm. The preferred average diameter depends on the intended use and preferred administration. For instance, in case the fibers are intended for use as an injectable drug delivery system, in particular as an ocular drug delivery system, an average diameter of 50-500 μm may be desired, more preferably an average diameter of 100-300 μm may be desired. Preferably the fibers are shaped and sized for injection in a needle ranging in size from 30 gauge to 12 gauge.

The core-shell system is composed of a polymer cylindrical core and a polymer shell with thickness between 0.5 and 5 μm. The two ends of the core can completely open or sealed at one end or at two ends in order to control drug release kinetics. Preferably the two ends of the core are completely open. When a small degree of drug burst is desired such as immediate effect on IOP similar to eye drops, the drug can also be present in the shell.

The drug delivery systems of the present invention may be used as a delivery system for drugs or bioactive agents. The system provides additional advantages for the delivery of acid sensitive drugs.

The drug delivery systems according to the present invention may comprise one or more bioactive agents.

As used herein, the term "bioactive agent" refers to an agent which possesses therapeutic, prophylactic, or diagnostic properties in vivo, for example when administered to an animal, including mammals, such as humans. Examples of suitable therapeutic and/or prophylactic active agents include proteins, such as hormones, antigens, and growth factors; nucleic acids, such as antisense molecules; and smaller molecules, such as antibiotics, steroids, deconges- tants, neuroactive agents, anesthetics, sedatives, and antibodies, such as antibodies that bind to growth hormone receptors, including humanized antibodies, adjuvants, and combinations thereof. Examples of suitable diagnostic and/ or therapeutic active agents include radioactive isotopes and radioopaque agents. The active agent can include organic molecules such as a drug, peptide, protein, carbohydrate (including monosaccharides, oligosaccharides, and polysaccharides), nucleoprotein, mucoprotein, lipoprotein, synthetic polypeptide or protein, or a small molecule linked to a protein, glycoprotein, steroid, nucleic acid (any form of DNA, including cDNA, or RNA, or a fragment thereof), nucleotide, nucleoside, oligonucleotides (including antisense oligonucleotides), gene, lipid, hormone, vitamin, including vitamin C and vitamin E, or combination thereof. Representative therapeutic active agents include immunosuppressants, antioxidants, anesthetics, chemotherapeutic agents, steroids (including retinoids), hormones, antibiotics, antivirals, antifungals, antiproliferatives, antihistamines, anticoagulants, antiphotoaging agents, melanotropic peptides, nonsteroidal and steroidal anti-inflammatory compounds, antipsychotics, and radiation absorbers, including UN-absorbers. Other non-limiting examples of active agents include anti-infectives such as nitrofurazone, sodium propionate, antibiotics, including penicillin, tetracycline, oxytetracycline, chlorotetracycline, bacitracin, nystatin, streptomycin, neomycin, polymyxin, gramicidin, chloramphenicol, erythromycin, and azithromycin; sulfonamides, including sulfacetamide, sulfamethizole, sulfamethazine, sulfadiazine, sulfamerazine, and sulfisoxazole, and anti-virals including idoxuridine; antiallergenics such as antazoline, methapyritene, chlorpheniramine, pyrilamine prophenpyridamine, hydrocortisone, cortisone, hydrocortisone acetate, dexamethasone, dexamethasone 21-phosphate, fluocinolone, triamcinolone, medrysone, prednisolone, prednisolone 21-sodium succinate, and prednisolone acetate; desensitizing agents such as ragweed pollen antigens, hay fever pollen antigens, dust antigen and milk antigen; decongestants such as phenylephrine, naphazoline, and tetrahydrazoline; miotics and anticholinesterases such as pilocarpine, esperine salicylate, carbachol, diisopropyl fluorophosphate, phospholine iodide, and demecarium bromide; parasympatholytics such as atropine sulfate, cyclopentolate, homatropine, scopolamine, tropicamide, eucatropine, and hydroxyamphetamine; sympathomimetics such as epinephrine; sedatives and hypnotics such as pentobarbital sodium, phenobarbital, secobarbital sodium, codeine, (a-bromoisovaleryl) urea, carbromal; psychic energizers such as 3-(2-aminopropyl) indole acetate and 3-(2-aminobutyl) indole acetate; tranquilizers such as reserpine, chlorpromayline, and thiopropazate; androgenic steroids such as methyl-testosterone and fluorymesterone; estrogens such as estrone, 17-beta-estradiol, ethinyl estradiol, and diethyl stilbestrol; progestational agents such as progesterone, megestrol, melengestrol, chlormadinone, ethisterone, norethynodrel, 19-no rogesterone, norethindrone, medroxyprogesterone and 17-beta-hydroxyprogesterone; humoral agents such as the prostaglandins, for example $PGE_{f5}$ $PGE_2$ and $PGF_2$; antipyretics such as aspirin, sodium salicylate, and salicylamide; antispasmodics such as atropine, methantheline, papaverine, and methscopolamine bromide; antimalarials such as the 4-aminoquinolines, 8-aminoquinolines, chloroquine, and pyrimethamine, antihistamines such as diphenhydramine, dimenhydrinate, tripelennamine, pefhenazine, and chlorphenazine; cardioactive agents such as dibenzhydroflume thiazide, flumethiazide, chlorothiazide, and aminotrate, natural and synthetic bioactive peptides and proteins, including growth factors, cell adhesion factors, cytokines, and biological response modifiers.

The amount of bioactive agent to be incorporated in the drug delivery system will vary depending upon the particular bioactive agent, the desired effect of the bioactive agent at the planned release levels, and the time span over which the bioactive agent should be released.

The bioactive agent also can be mixed with one or more excipients, such as stabilizing agents, known in the art.

Examples of acid sensitive drugs are especially biopharmaceuticals including physiologically active protein or peptide species or hydrolytically sensitive molecules. Examples of biopharmaceuticals including physiologically active protein or peptide species are etanercept, ranibizumab, bevacizumab. Examples of hydrolytically sensitive molecules are latanoprost, bimatoprost and travoprost.

In accordance with the present invention, if a bioactive agent is present, it is preferably present in the core. The concentration of one or more bioactive agent(s) in the core can be determined by the therapeutic window of the treated medical indication as well as by an administration method. The concentration of one or more bioactive agent(s) in the core of the drug delivery system can be at least 1 wt %, based on the total weight of the drug delivery system, in particular at least 5 wt. %, more in particular at least 10 wt %. The concentration may be up to 90 wt %, up to 70 wt %, up to 50 wt. % or up to 30 wt. %, as desired.

Polymer X or Y and the bioactive agent or acid sensitive drug are preferably solvent blended, the selection of the solvent used generally depends on the polymer and bioactive agent chosen, as well as the particular means of solvent removal to be employed. Examples of solvents are acetone, methyl ethyl ketone, tetrahydrofuran, ethyl lactate, ethyl acetate or dichloromethane.

In addition to the polymers X and Y, the drug delivery system of the present invention may further comprise in the core or in the shell one or more other polymers selected from the group of other biocompatible polymers.

Examples of biocompatible polymers are poly(anhydrides), poly(phospho esters), poly(trimethylene carbonate), poly(oxa-esters), poly(oxa-amides), poly(ethylene carbonate), poly(propylene carbonate), poly(phosphoesters), poly(phosphazenes), poly(tyrosine derived carbonates), poly(tyrosine derived arylates), poly(tyrosine derived iminocarbonates), copolymers of these polymers with poly(ethylene glycol) (PEG), or combinations thereof.

The present invention also relates to a process for the manufacturing of the drug delivery systems of the present invention via a 2-steps process comprising a melt processing step and a coating step. Alternatively it can also be manufactured via a 1-step process especially via co-extrusion.

Especially for the manufacturing of the fibers there are three common methods available such as wet spinning, dry spinning and melt spinning. Wet spinning involves extruding a solution of a polymer through an orifice into a nonsolvent to coagulate the polymer. In the dry-spinning process, a solution of a polymer is forced through an orifice and fed into a heated column that evaporates the solvent to form a filament. In melt-spinning, a thermoplastic polymer is heated above its melting point, extruded through an orifice, and cooled to form a filament. With coaxial spinning, the drug is extruded as the core of the fiber at the same time as the rate-controlling polymer shell. A typical coaxial spinneret consists of two concentric rings. The drug, either in pure form or dispersed within a polymeric matrix, is pumped through the inner ring, where it forms the core. The rate-controlling polymer is pumped through the outer ring to form the shell. As both streams of material emerge from the spinneret, they solidify to form the coaxial fiber or reservoir system. The rate at which the two polymers are pumped to the coaxial spinneret determines the thickness of the shell and the size of the fiber.

The polymer or drug is liquefied for extrusion either by melting or dissolution in a solvent. A preferred method is melt extrusion in which two extruders are used to process the core and the shell. The core formulation is fed to the center tube of a coaxial die and the shell polymer is fed to a concentric outer ring of the same die such that the shell polymer forms a uniform coating on the core as the polymers exit the die. The relative diameters of the core and shell are controlled by the dimensions of the die, the extrusion conditions, the relative extrusion rates of the two extruders, and the relative take-off speed. In this way, the core diameter and shell thickness can be independently controlled.

Another method of preparing the fibers of the present invention is to first prepare a core formulation by a simple extrusion process and then form the shell by a surface treatment of the core. The surface treatment may be accomplished by annealing the surface by exposure to elevated temperature or to a solvent for the polymer excipient so that the polymer forms a thin skin at the surface, which then functions as a rate controlling shell. The shell also may be added by applying a coating of the shell formulation by a solution coating process. The solution coating process could be used to apply additional layers of different compositions thereby constructing multilayer coaxial fibers.

Yet another method of preparing the fibers of the present invention is to first prepare the shell as an empty tube, and then add the core formulation by injecting it into the center of the tube. As an example, the core formulation may consist of drug incorporated into a liquid polymer matrix. Although generally formed in a geometry where the cross-section is a circle, the fiber can also be prepared with any other cross-sectional geometry, for example, an ellipsoid, a lobe, a square, or a triangle.

The drug can be added to the formulation in a variety of ways. If the core formulation contains a polymer, the drug and polymer can be mixed by solvent-blending, dry blending, or melt blending. More uniform mixing may be obtained by extruding the drug-matrix twice. In the preferred embodiment, the core is formulated by dry blending the drug and polymer, melt extruding the blend, and grinding the extrudate to form a feedstock for the second extrusion.

The final drug delivery system is formed by cutting the core/shell formulation to the appropriate length for the desired dose and sealing the exposed ends of the core. In a preferred embodiment, an initial loading dose may be desired, which can be accomplished for certain drugs by sealing only one or neither of the exposed ends so that there is a brief period of higher release. Several methods can be used to seal the ends of the drug delivery system. If the drug delivery system contains a solid core it can be sealed by coating with a solution of the shell polymer or by applying the molten shell polymer, or simply by cutting the drug delivery system with a hot knife or wire such that it is heat sealed as the cut is made. If the drug delivery system contains a liquid core, the ends may be heat sealed, or they may be sealed by placing a polymer plug into the lumen of the shell formulation. When a polymer plug is used, it may be optionally heat sealed to the shell. The drug delivery systems may be prepared in a variety of sizes depending on the total dose of drug and the envisioned method of administration. In a preferred embodiment, the overall diameter is between 0.05 and 5.0 mm. For subcutaneous administration in humans, an overall diameter of between 1.0 and 4.0 mm preferably between 0.2 and 2 mm may be used. The length of the drug delivery system is typically between 0.5 mm and 20 mm. Preferably the length is between about 1 mm and 10 mm, a more preferred length is between 2 mm and 8 mm, even more preferably between 2 mm and 6 mm.

The present invention also relates to a method for treating glaucoma, ocular hypertension and other indications associated with raised intraocular pressure by administering bioactive agents to the eye with the drug delivery system according to the present invention. Other indications associated with raised intraocular pressure are for example diabetic retinopathy or macular degeneration.

The present invention further relates to the drug delivery system for use as a medicament.

The present invention also relates to the drug delivery system according to the present invention for use in the treatment of glaucoma, ocular hypertension, diabetic retinopathy or macular degeneration.

Preferably the drug delivery system is a fiber which is preferably manufactured via an extrusion process for example melt extrusion in which the biodegradable polymer and eventual additional compounds are homogenized using a Retsch® cryomill. The resulting powder is then filled into a pre-heated micro-extruder with 5 cc barrel size and twin-screws which are connected to a micro fiber spin device. The biodegradable polymer preferably has a residence time of 5-10 min at 120 C-140° C. before it is to be stretched into a fiber with diameter in the range of 100-250 µm. The extrusion is normally performed under inert atmosphere in order to minimize the oxidative degradation of the polymer during the process. Under tension it is subsequently cooled at room temperature. Preferably fibers of 1-6 cm length are cut from the fiber roll and polymer coatings are applied by dip-coating or spray coating. In a dip coating process the fibers are clamped and immersed in a polymer solution bath at a controlled speed (for example, 1.5 cm/s). Afterwards they are dried in a controlled environment (20° C., 40% RH). In a spray-coating process, the fibers are fixed on a horizontal rotating support and sprayed from the top with polymer solutions in a controlled environment (20° C., 40% RH). Polymer solutions are pumped at specific flow rates (for example, 0.1 mL/min) through an ultrasonic nozzle to create a soft velocity spray to be applied on the rotating fiber. The obtained fiber is then preferably cut into pieces from for example 5 mm, creating fibers with open ends. The fiber may be sterilized via gamma radiation under cooling conditions.

Alternatively, the fibers of the present invention can also be prepared via injection molding. In this process fibers are formed in an injection molder at temperature 100-200° C. resulting in fibers with a diameter of approximately 200 µm. Then the mold is cooled to room temperature before opening and the fibers are taken out. Essential for this processing method is that so obtained fibers do not re-model upon exposure to aqueous environment well preserving their length and diameter. Preferably fibers of 1-6 cm length are cut and polymer coatings are applied by dip-coating or spray coating. The obtained fiber is then preferably cut into pieces from for example 5 mm, creating fibers with open ends. The fiber may be sterilized via gamma radiation under cooling conditions.

In accordance with the invention it is possible to provide fibers with one or more bioactive agents with satisfactory encapsulation efficiency. (i.e. the amount of bioactive agent in the fibers, divided by the amount of active agent used). Depending upon the loading conditions, an efficiency of at least 20%, an efficiency of at least 50%, at least 75% or at least 90% or more is feasible.

The fibers may be incorporated into for example (rapid prototyped) scaffolds, coatings, patches, composite materials, gels, plasters or hydrogels. Alternatively, other structures such as particles can be incorporated into fibers to create composite systems.

The fibers according to the present invention can be injected or implanted. In a particular embodiment the fiber is injectable in the subjunctival space of the eye.

In a further embodiment, the fibers may be imageable by a specific technique such as MRI, CT, X-ray. The imaging agent can be incorporated inside the core or shell of the fibers or can be coupled onto the surface of the shell. A suitable imaging agent is for example gadolinium.

The fibers comprising the polyesteramide copolymers according to the present invention can be used in the medical field especially in drug delivery in the field of management of ophthalmology.

The fiber according to the present invention can be used as a drug eluting vehicle especially for the treatment of glaucoma.

The present invention will now be described in detail with reference to the following non limiting examples and figures which are by way of illustration only.

The present invention will be further understood by reference to the following non-limiting examples.

FIGURES

FIG. 1: shows cumulative release percentages of Latanoprost indicating constant drug release for the PEA-III-X25 core-shell fiber, while the PEA-III-X25 core, no shell exhibits a burst release. daily doses of Latanoprost are presented with a fiber comprising no shell displaying significant burst in the first 20 days of the release.

FIG. 2: shows the release of Latanoprost in daily doses with a fiber comprising no shell displaying significant burst in the first 20 days of the release.

FIG. 3: shows the release of Latanoprost with a constant daily dose of Latanoprost of 0.05 µg/day during 140 days.

FIG. 4: show cumulative release curves and daily doses for PEA-III-AcBz and PEAIIIX25 cores. The results show a decrease in daily doses over time due the non-degradation PEA-III-AcBz polymer core during the release time scale.

FIG. 5: show cumulative release curves and daily doses for PEA-III-AcBz and PEA-III-X25 cores. The results show a decrease in daily doses over time due the non-degradation PEA-III-AcBz polymer core during the release time scale.

FIG. 6: show cumulative release curves and daily doses of Latanoprost from PLGA and show poor control over daily doses with high Latanoprost burst when the polymer matrix is degraded.

FIG. 7: show cumulative release curves and daily doses of Latanoprost from PLGA and show poor control over daily doses with high Latanoprost burst when the polymer matrix is degraded.

FIG. 8: show that core shell fibers made of PEA-III-X25 and PEA-III-AcBz do not reduce burst effect, exhibiting a similar drug release profile as fibers comprising no shell.

FIG. 9: show that core shell fibers made of PEA-III-X25 and PEA-III-AcBz do not reduce burst effect, exhibiting a similar drug release profile as fibers comprising no shell.

FIG. 10: shows the morphology of the fiber after 1 week.

Figure 14:
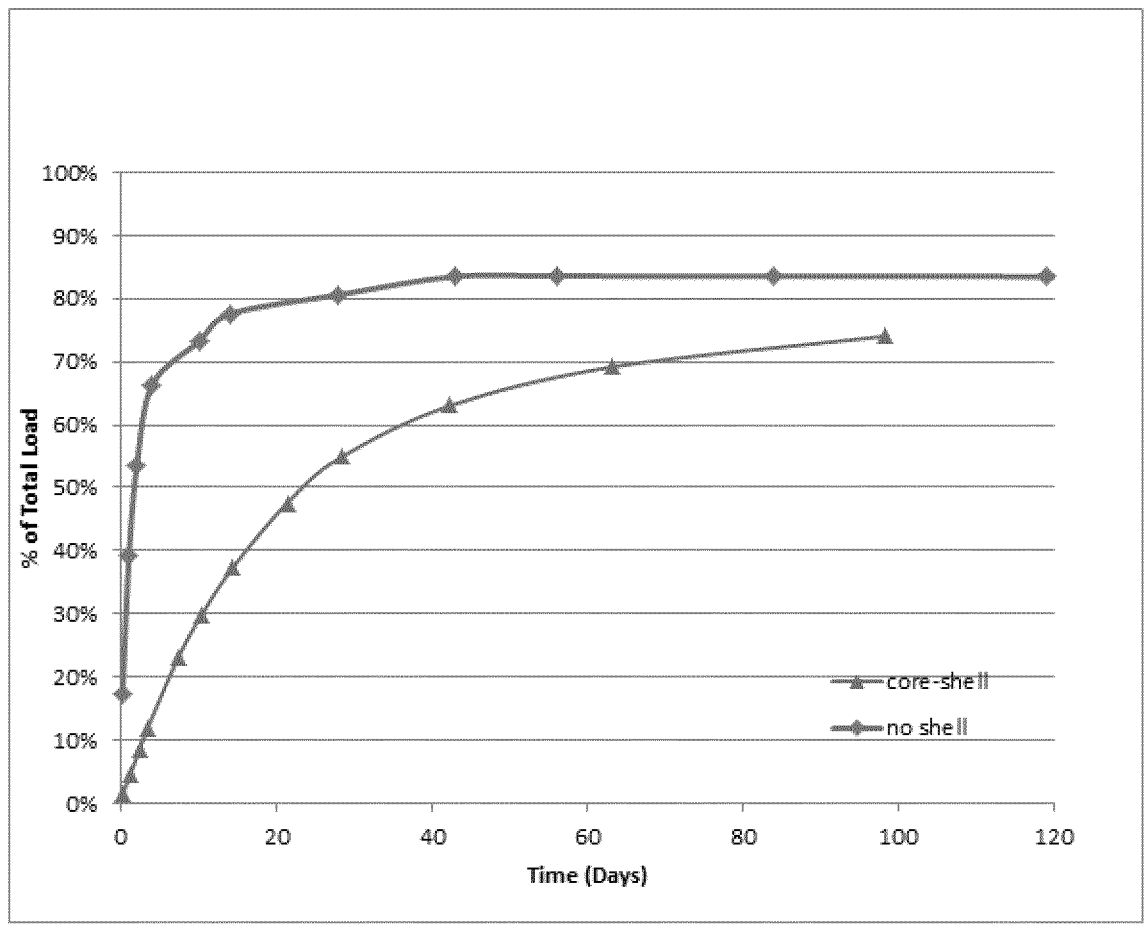

FIG. 14: shows cumulative release percentages of bimatoprost indicating controlled drug release for the PEA-III-X25 core-shell fiber, while the PEA-III-X25 core, no shell exhibits a burst release.

Figure 15:
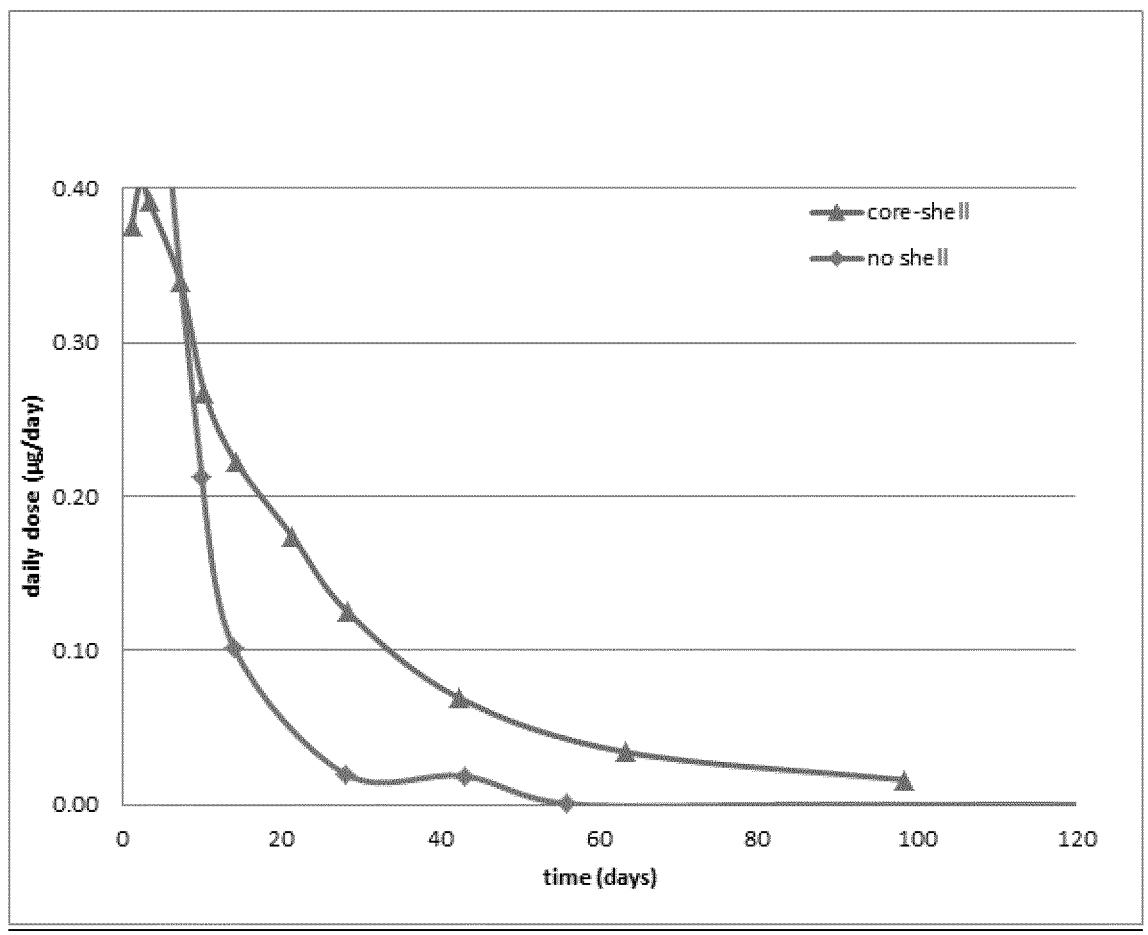

FIG. 15: shows daily doses of bimatoprost with a fiber comprising no shell displaying significant burst in the first 10 days of release.

EXAMPLES

Example 1

Figure 1:
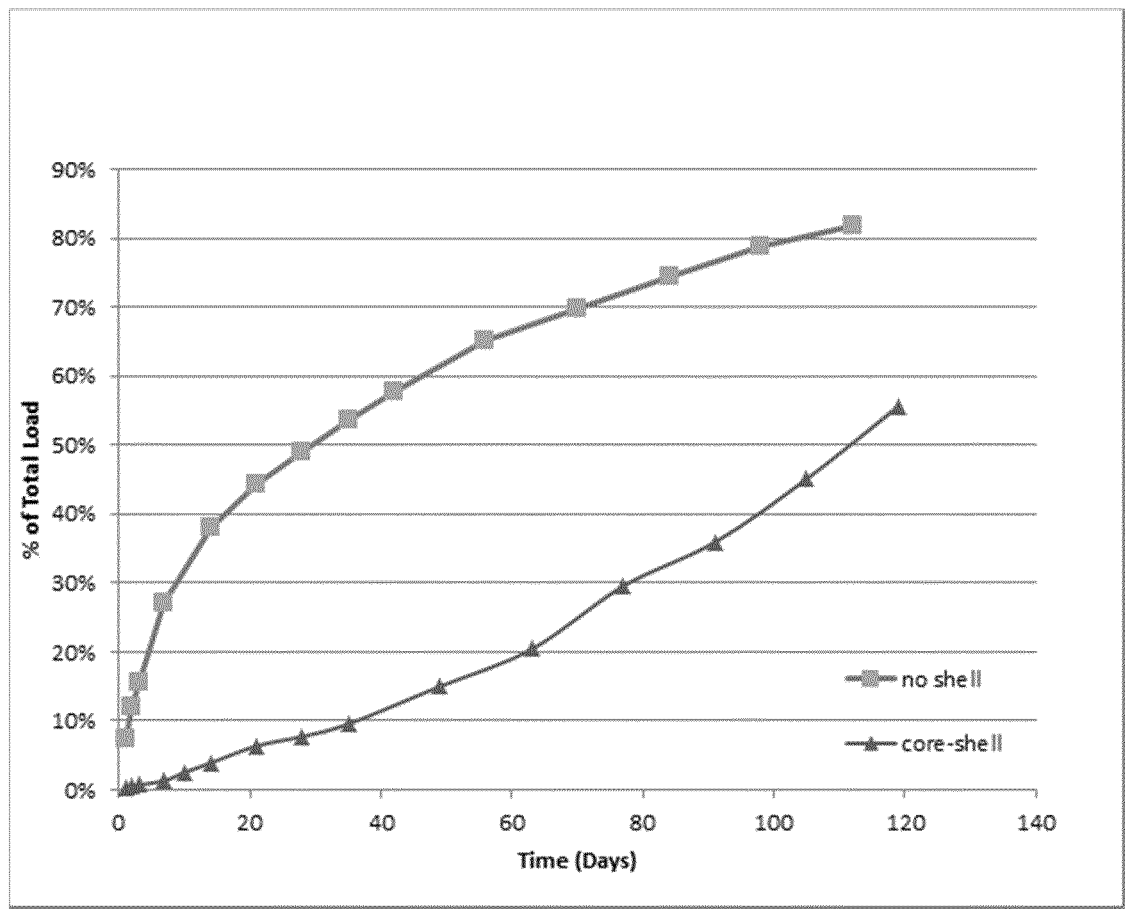
Figure 2:
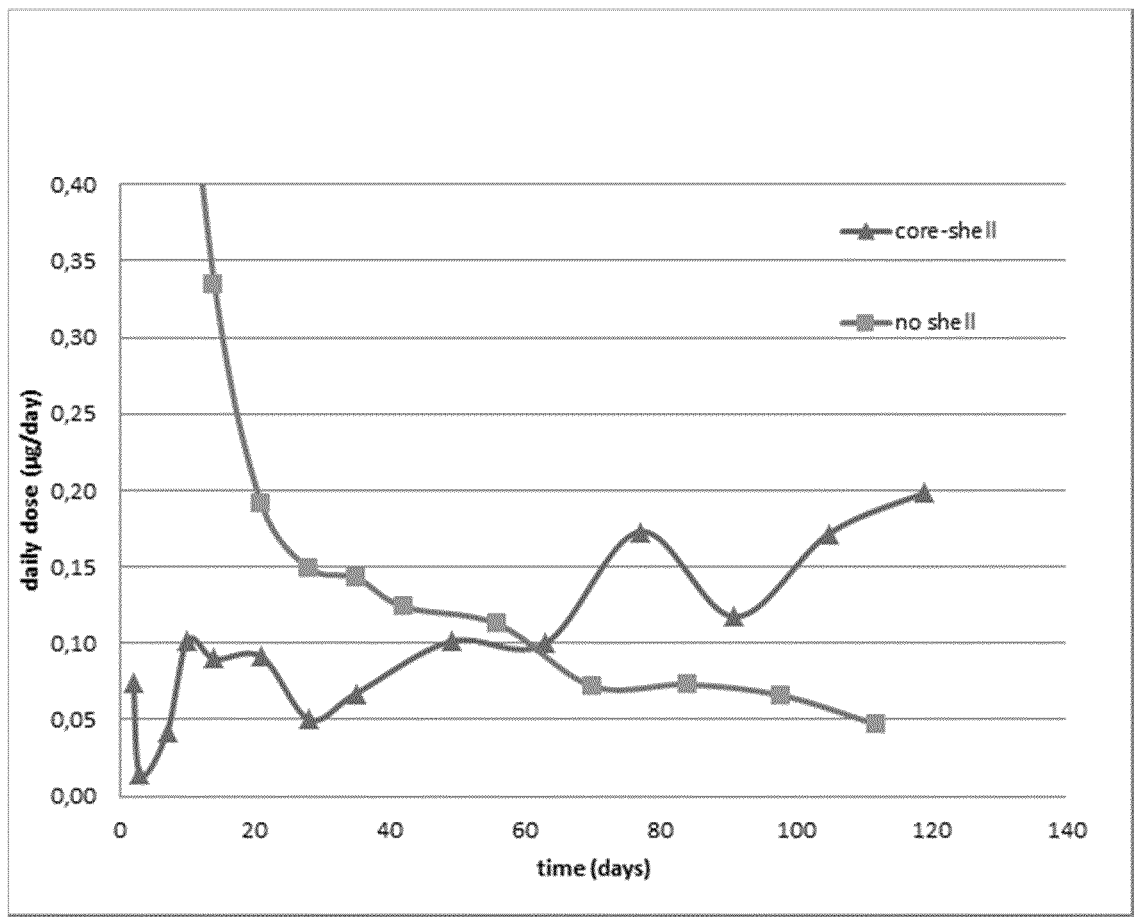

Latanoprost Release from Core Shell Fibers Comprising PEA-III-X25/PLGA and Fibers of PEA-III-X25 Comprising No Shell Fibers made of PEA-III-X25 with a loading percentage of 10% latanoprost were prepared by extrusion and coated with PLGA. Four individual fibers with a diameter of 240 µm and 5 mm long were placed in 1.2 ml PBS buffer solution at 37° C. At varying time points 0.9 mL PBS solution was refreshed to assure sink conditions and the drug concentration was subsequently measured. Typically, samples were measured every day in the first week and weekly at later time points. For the quantitative analysis of the release of latanoprost samples a Waters e2695 Alliance HPLC with a photodiode array detector was used. An isocratic HPLC method was used with a Agilent Zorbax Eclipse XBD-C18 4.6×250 mm, 5 µm column. The mobile phase was Acetonitrile/$H_2O$ (60/40 containing 0.05% TFA) and the flow was 1.0 ml/min. Column temperature was set to 25° C. and sample temperature to 15° C. Samples were measured at a wavelength of 210 nm. The system of Latanoprost showed linearity in a range of 1 µg-200 µg which was also the range used for a standard calibration curve. FIG. 1 shows cumulative release percentages of latanoprost indicating constant drug release for the PEA-III-X25 core-shell fiber, while the PEA-III-X25 core, no shell exhibits a burst release. In FIG. 2 daily doses of latanoprost are presented with a fiber comprising no shell displaying significant burst in the first 20 days of release.

Example 2

Latanoprost Release from PEA-III-X25/PLLA Core-Shell Fibers

Figure 3:
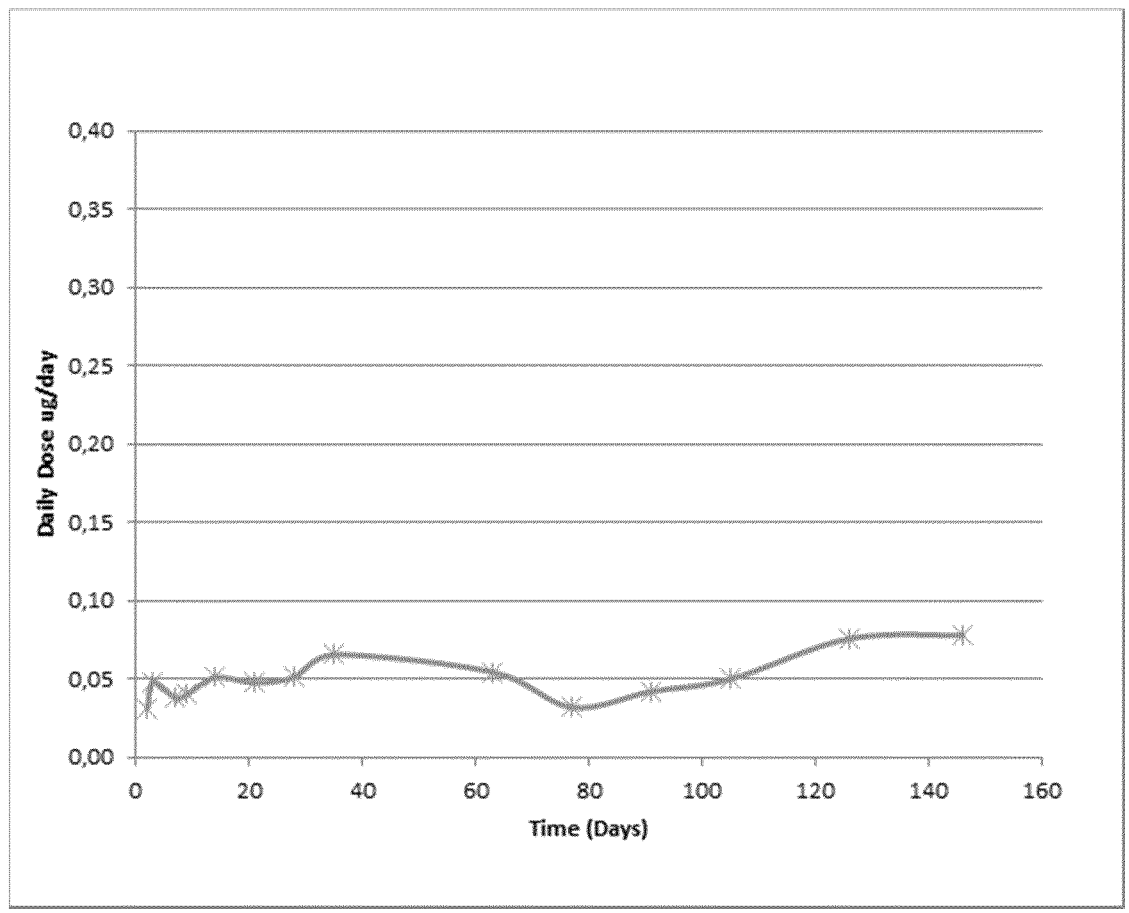

Fibers made of PEA-III-X25 with a loading percentage of 15% latanoprost were prepared by melt injection and coated with PLLA. Four individual fibers with a diameter of 200 µm and 5 mm long were placed in 1.2 ml PBS buffer solution at 37° C. At varying time points 0.9 mL PBS solution was refreshed to assure sink conditions and the drug concentration was subsequently measured. FIG. 3 shows a constant daily dose of latanoprost of 0.05 µg/day during 140 days.

Example 3

Latanoprost Release from Core Shell Fibers Comprising PEA-III-X25/PEA-111-X25, PEA-III-X25/PEA-III-AcBz Core-Shell and Fibers of PEA-III-X25 Comprising No Shell Fibers made of PEA-III-X25 with a loading percentage of 10% latanoprost were prepared by melt injection and coated with PEA-III-X25 and PEA-III-AcBz. Three individual fibers with a diameter of 200 µm and 5 mm long were placed in 1.2 ml PBS buffer solution at 37° C. At varying time points 0.9 mL PBS solution was refreshed to assure sink conditions and the drug concentration was subsequently measured.

Figure 8:
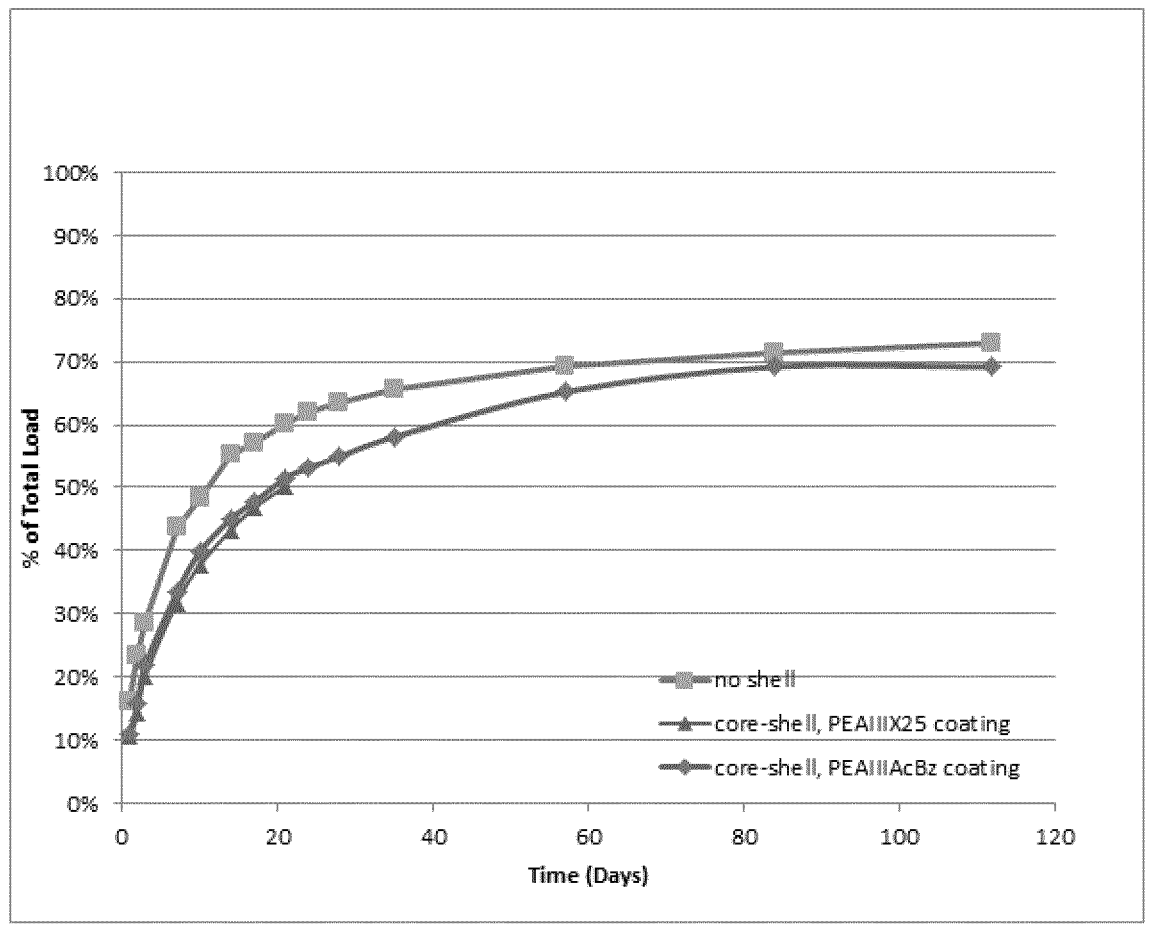
Figure 9:
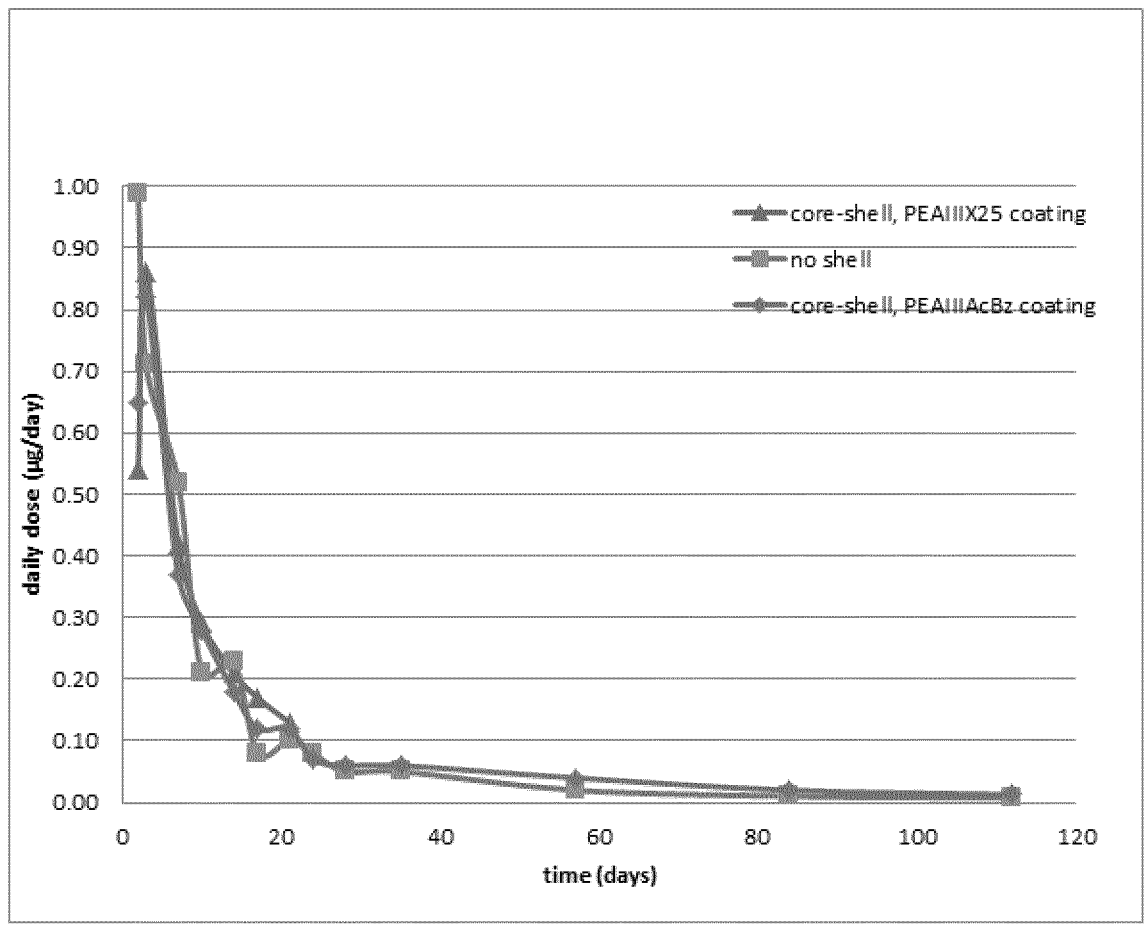
Figure 10:
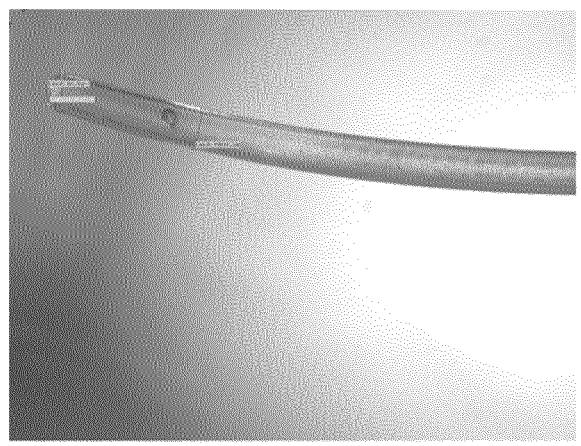
Figure 11:
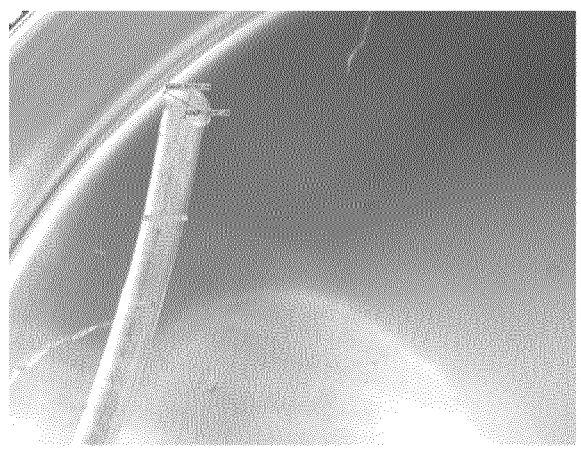
FIG. 11 shows the morphology of the fiber after c1 month.
Figure 12:
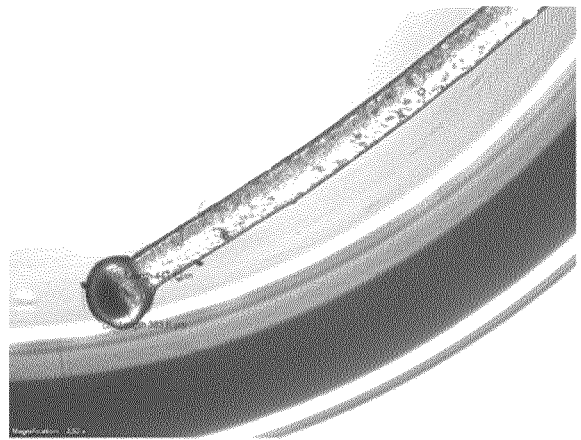
FIG. 12 shows the morphology of the fiber after 3 months.
Figure 13:
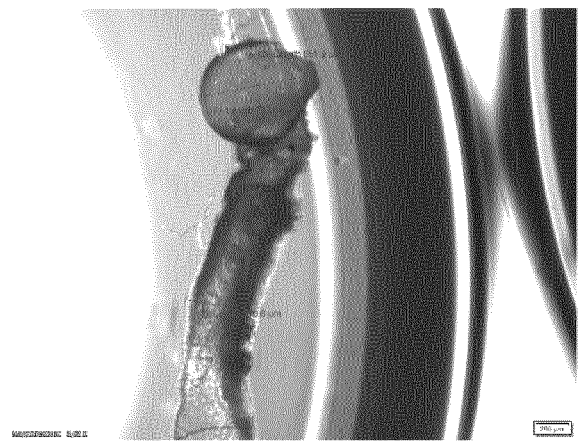
FIG. 13 shows the morphology of the fiber after 8 months.

FIG. 8 and FIG. 9 show that core shell fibers made of PEA-III-X25 and PEA-III-AcBz do not reduce burst effect, exhibiting a similar drug release profile as fibers comprising no shell.

Example 4

PEA-III-X25/PLGA Core-Shell Fibers During Drug Release

Fibers made of PEA-III-X25 with a loading percentage of 15% latanoprost were prepared by injection molding and coated with PLGA. Four individual fibers were placed in 1.4 ml PBS buffer solution at 37° C. At selected timepoints, fibers were imaged immersed in PBS using a Olympus CX-41 light microscope at 4× magnification. FIGS. 10-13 show the morphology of the fiber at 1 week, 1 month, 3 months and 8 months. As the PEA-III-X25 core degrades and leaches out of the coating, the surface area of the fiber ends increases, increasing the surface available for drug diffusion. The observed effect compensates for the decrease in the drug concentration gradient, producing a more constant drug release profile.

Example 5

Bimatoprost Release from PEA-III-X25/PLLA Core-Shell Fibers

Fibers made of PEA-III-X25 with a loading percentage of 30% bimatoprost were prepared by melt injection and coated with PLLA. Five individual fibers with a diameter of 200 µm and 1.2 mm long were placed in 0.25 ml PBS buffer solution at 37° C. At varying time points 0.15 mL PBS solution was refreshed to assure sink conditions and the drug concentration was subsequently measured. FIG. 14 shows cumulative release percentages of bimatoprost indicating controlled drug release for the PEA-III-X25 core-shell fiber, while the PEA-III-X25 core, no shell exhibits a burst release. In FIG. 15 daily doses of bimatoprost are presented with a fiber comprising no shell displaying significant burst in the first 10 days of release.

Comparative Experiment A: Latanoprost release from PEA-III-AcBz/PLGA, PEA-III-X25/PLGA Core-Shell and PEA-III-AcBz No Shell Systems Fibers made of PEA-III-AcBz [(poly-8-[(L-Leu-DAS)$_{0.45}$(L-Leu-6)$_{0.3}$-[L-Lys(Bz)]$_{0.25}$.] structure is given in Formula III with a loading percentage of 10% latanoprost were prepared by extrusion and coated with PLGA. PEA-III-X25 fibers with a loading percentage of 10% latanoprost were prepared by extrusion and coated with PLGA. Four individual fibers with a diameter of 250 µm and 5 mm long were placed in 1.2 ml PBS buffer solution at 37° C. At varying time points 0.9 mL PBS solution was refreshed to assure sink conditions and the drug concentration was subsequently measured.

Figure 4:
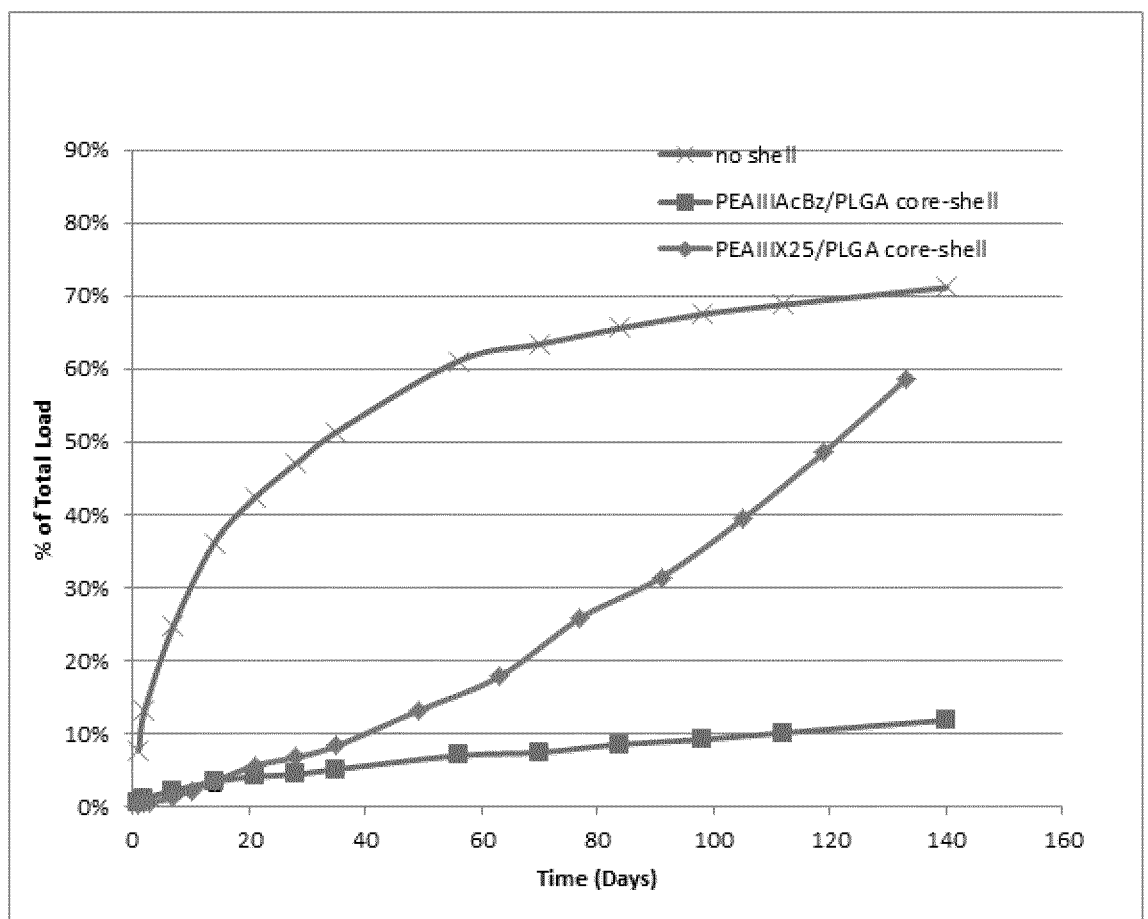
Figure 5:
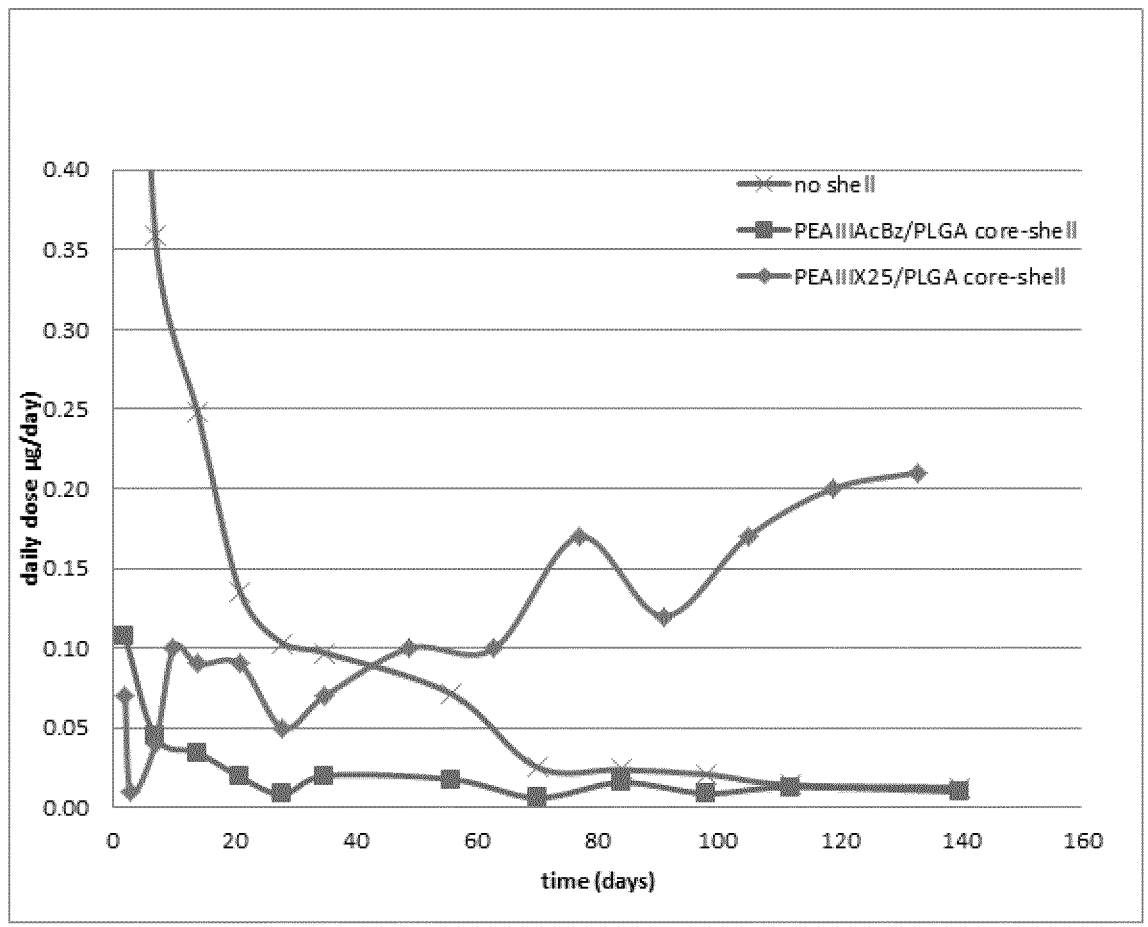

FIG. 4 and FIG. 5 present cumulative release curves and daily doses for PEA-III-AcBz and PEA-III-X25 cores. The results show a decrease in daily doses over time due the non-degradation PEA-III-AcBz polymer core during the release time scale. In contrast, fibers made of PEA-III-X25 show an increase in daily dose due to polymer degradation.

Formula III

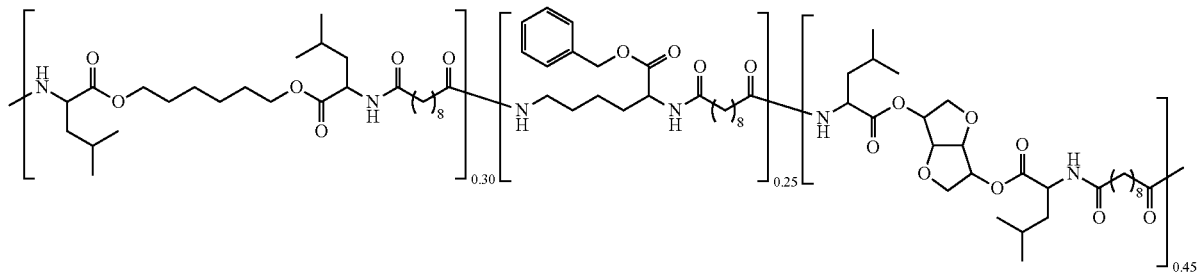

Comparative Experiment B: Latanoprost Release from PLGA Disks

Figure 6:
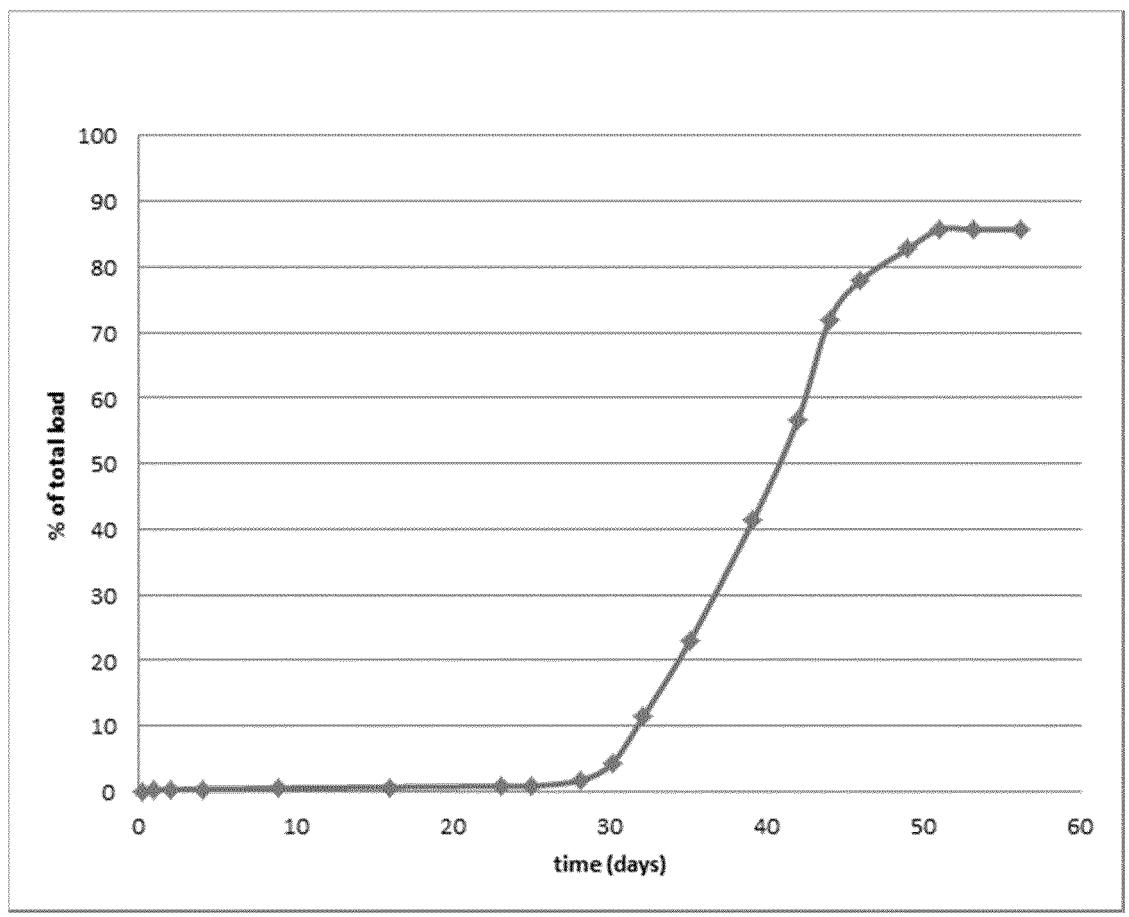
Figure 7:
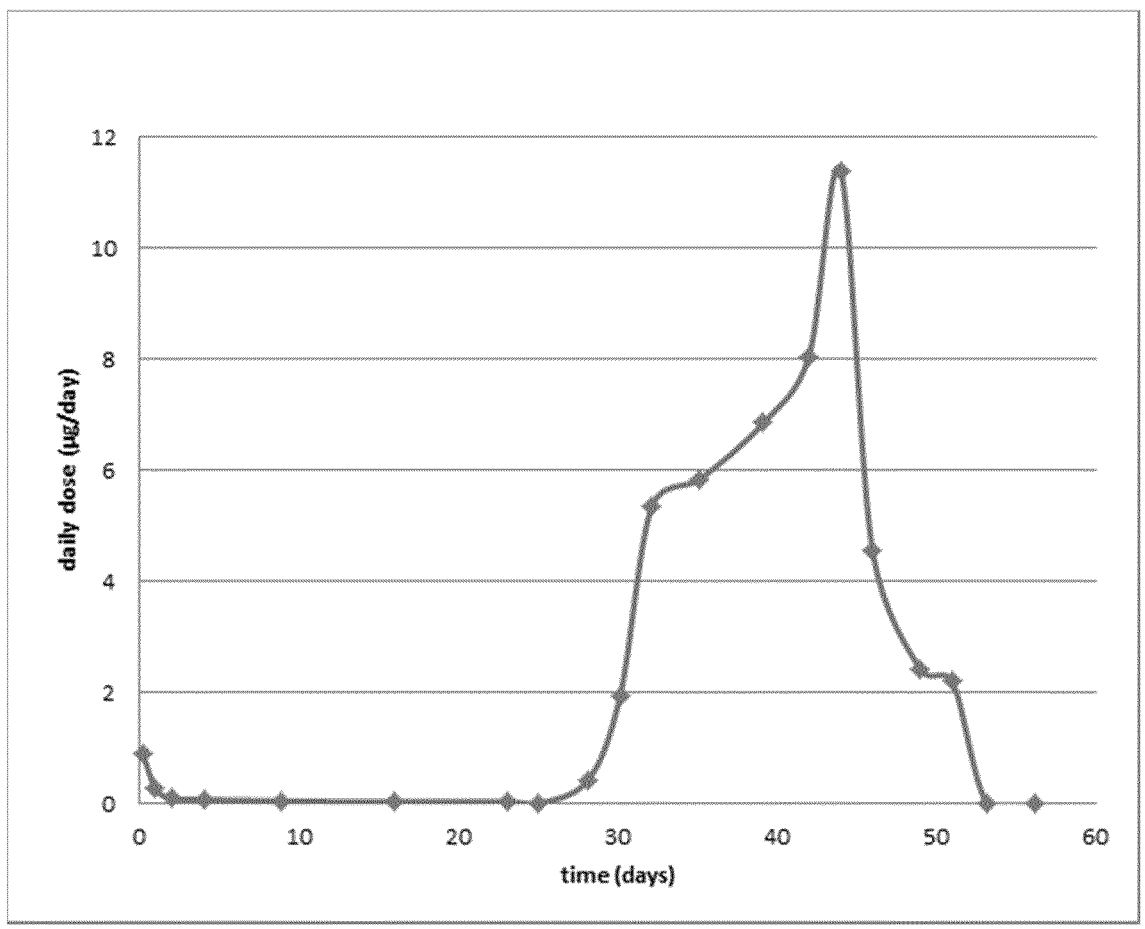

Drug loaded disks of PLGA with a loading percentage of 10% latanoprost were prepared by solvent casting films and punching out samples from the films. Three individual disks with a diameter of 7 mm were placed in 5.0 ml PBS buffer solution at 37° C. At varying time points the complete PBS solution was refreshed to assure sink conditions and the drug concentration was subsequently measured. FIG. 6 and FIG. 7 present cumulative release curves and daily doses of latanoprost from PLGA and show poor control over daily doses with high latanoprost burst when the polymer matrix is degraded.

The invention claimed is:

1. A fiber for the delivery of a bioactive agent to an eye of a mammal, the fiber comprising a cylindrical core and a shell partially surrounding the core, the core comprising a bioactive agent and a polyesteramide copolymer according to the following chemical formula:

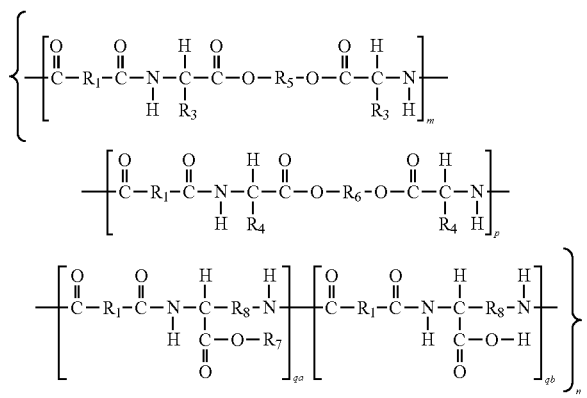

wherein
m+p is from 0.9 to 0.1 and q is from 0.1 to 0.9;
m+p+q=1 whereby one of m or p could be 0;
n is about 5 to about 300;
a is at least 0.05, b is at least 0.05, a+b=1, qa=q*a, and qb=q*b; wherein units of
m if present, units of p if present, units of qa, and units of
qb are all randomly distributed throughout the copolymer;
$R_1$ is $(C_2-C_{20})$ alkylene;
$R_3$ and $R_4$ are independently selected from hydrogen, $(C_1-C_6)$alkyl, $(C_2-C_6)$alkenyl, $(C_2-C_6)$alkynyl, $(C_6-C_{10})$aryl, $-CH_2SH$, $-(CH_2)_2S(CH_3)$, $-CH_2OH$, $-CH(OH)CH_3$, $-(CH_2)_4NH_3+$, $-(CH_2)_3NHC(NH_2+)NH_2$, $-CH_2COOH$, $-CH_2-CO-NH_2$, $-CH_2CH_2-CO-NH_2$, $-CH_2CH_2COOH$, $CH_3-CH_2-CH(CH_3)-$, $(CH_3)_2CH-CH_2-$, $H_2N-(CH_2)_4-$, $Ph-CH_2-$, $CH=C-CH_2-$, $(CH_3)_2CH-$, or $Ph-NH-$;
$R_5$ is $(C_2-C_{20})$alkylene;
$R_6$ is structural formula (III);

Formula III

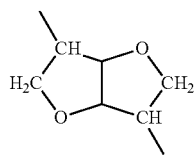

$R_7$ is $(C_6-C_{10})$aryl$(C_1-C_6)$alkyl;
$R_8$ is $-(CH_2)_4-$; and
the shell comprising a hydrolytically degradable polymer, the hydrolytically degradable polymer comprising poly(lactic acid), poly(glycolic acid), poly(lactide-co-glycolide), polycaprolactone, or a combination thereof.

2. The fiber according to claim 1, wherein $R_3$ and $R_4$ are independently hydrogen, $(C_1-C_6)$alkyl, $CH_3-CH_2-CH(CH_3)-$, $(CH_3)_2CH-CH_2-$, $Ph-CH_2-$, or $(CH_3)_2CH-$.

3. The fiber according to claim 1, wherein the polyesteramide copolymer comprises at least pendant 15% acid groups based on the total amount of pendant functionalities of the polyesteramide copolymer.

4. The fiber according to claim 1, wherein the bioactive agent is an acid sensitive bioactive agent.

5. The fiber according to claim 1, wherein the bioactive agent comprises latanoprost, bimatoprost or travoprost.

6. The fiber according to claim 1, wherein n is from 50 to 200, a is at least 0.15.

7. The fiber according to claim 1, wherein n is from 50 to 200, a is at least 0.5.

8. The fiber according to claim 1, wherein n is from 50 to 200, a is at least 0.75.

9. The fiber according to claim 1, wherein n is from 50 to 200, a is at least 0.8.

10. The fiber according to claim 2, wherein n is from 50 to 200, a is at least 0.15.

11. The fiber according to claim 2, wherein n is from 50 to 200, a is at least 0.5.

12. The fiber according to claim 1, wherein $R_3$ and $R_4$ are $(CH_3)_2CH-CH_2-$; and $R_7$ is benzyl.

13. The fiber according to claim 1, wherein $R_1$ is $-(CH_2)_8-$; $R_3$ and $R_4$ are $(CH_3)_2CH-CH_2-$; and $R_7$ is benzyl.

14. The fiber according to claim 7, wherein $R_3$ and $R_4$ are $(CH_3)_2CH-CH_2-$; and $R_7$ is benzyl.

15. The fiber according to claim 7, wherein $R_1$ is $-(CH_2)_8-$; $R_3$ and $R_4$ are $(CH_3)_2CH-CH_2-$; and $R_7$ is benzyl.

16. The fiber according to claim 1, wherein the cylindrical core comprises a side and two ends, and wherein the shell surrounds the side and one end of the cylindrical core, and the shell does not surround the other end of the cylindrical core.

17. The fiber according to claim 1, wherein the cylindrical core comprises a side and two ends, and wherein the shell surrounds the side of the cylindrical core, and the shell does not surround the ends of the cylindrical core.

18. The fiber according to claim 14, wherein the cylindrical core comprises a side and two ends, and wherein the shell surrounds the side of the cylindrical core, and the shell does not surround the ends of the cylindrical core.

19. The fiber according to claim 1, wherein the fiber has an average diameter of from 50 to 500 μm and the shell has a thickness of between 0.5 and 5 μm.

20. The fiber according to claim 1, wherein the core consists of the polyesteramide copolymer, the bioactive agent, and optionally an excipient.

21. The fiber according to claim 1, wherein the shell consists of poly(lactic acid), poly(glycolic acid), poly(lactide-co-glycolide), polycaprolactone, or a combination thereof.

22. The fiber according to claim 14, wherein the shell consists of poly(lactic acid), poly(glycolic acid), poly(lactide-co-glycolide), polycaprolactone, or a combination thereof.

23. The fiber according to claim 14, wherein the bioactive agent comprises latanoprost, bimatoprost or travoprost.

24. The fiber according to claim 22, wherein the bioactive agent comprises latanoprost, bimatoprost or travoprost.

25. A method for treating glaucoma, ocular hypertension, diabetic retinopathy or macular degeneration comprising the step of injecting the fiber according to claim 1 into the eye or subconjunctival space of a mammal in need of treatment thereof.

26. A method for treating glaucoma, ocular hypertension, diabetic retinopathy or macular degeneration comprising the step of injecting the fiber according to claim 5 into the eye or subconjunctival space of a mammal in need of treatment thereof.

27. A method for treating glaucoma, ocular hypertension, diabetic retinopathy or macular degeneration comprising the step of injecting the fiber according to claim 23 into the eye or subconjunctival space of a mammal in need of treatment thereof.

28. A method for treating glaucoma, ocular hypertension, diabetic retinopathy or macular degeneration comprising the step of injecting the fiber according to claim 24 into the eye or subconjunctival space of a mammal in need of treatment thereof.

* * * * *